(12) United States Patent
Kaymakcalan et al.

(10) Patent No.: US 8,846,046 B2
(45) Date of Patent: Sep. 30, 2014

(54) LOW DOSE METHODS FOR TREATING DISORDERS IN WHICH TNFα ACTIVITY IS DETRIMENTAL

(75) Inventors: Zehra Kaymakcalan, Westborough, MA (US); Robert Kamen, Sudbury, MA (US)

(73) Assignee: AbbVie Biotechnology Ltd., Hamilton (BM)

( * ) Notice: Subject to any disclaimer, the term of this patent is extended or adjusted under 35 U.S.C. 154(b) by 0 days.

(21) Appl. No.: 10/693,233

(22) Filed: Oct. 24, 2003

(65) Prior Publication Data

US 2004/0166111 A1    Aug. 26, 2004

Related U.S. Application Data

(60) Provisional application No. 60/421,262, filed on Oct. 24, 2002.

(51) Int. Cl.
*A61K 39/395* (2006.01)
*C07K 16/24* (2006.01)
*A61K 39/00* (2006.01)
*A61K 38/17* (2006.01)

(52) U.S. Cl.
CPC ......... *C07K 16/241* (2013.01); *A61K 2039/545* (2013.01); *C07K 2317/92* (2013.01); *A61K 38/1793* (2013.01); *A61K 2039/505* (2013.01)
USPC ..................................................... 424/145.1

(58) Field of Classification Search
USPC ............... 424/130.1, 141.1, 142.1, 145.1; 530/387.1, 388.1, 388.15, 388.23
See application file for complete search history.

(56) References Cited

U.S. PATENT DOCUMENTS

| | | | |
|---|---|---|---|
| 4,597,966 A | 7/1986 | Zolton et al. | |
| 4,897,465 A | 1/1990 | Cordle et al. | |
| 5,231,024 A | 7/1993 | Moeller et al. | |
| 5,237,054 A | 8/1993 | Brinks et al. | |
| 5,608,038 A | 3/1997 | Eibl et al. | |
| 5,654,403 A | 8/1997 | Smith et al. | |
| 5,698,195 A | 12/1997 | Le et al. | |
| 5,792,838 A | 8/1998 | Smith et al. | |
| 5,795,967 A | 8/1998 | Aggarwal et al. | |
| 5,859,205 A | 1/1999 | Adair et al. | |
| 5,877,293 A | 3/1999 | Adair et al. | |
| 5,929,212 A | 7/1999 | Jolliffe et al. | |
| 5,945,098 A | 8/1999 | Sarno et al. | |
| 5,994,510 A | 11/1999 | Adair et al. | |
| 5,998,378 A | 12/1999 | Kriegler | |
| 6,015,557 A | 1/2000 | Tobinick et al. | |
| 6,024,938 A | 2/2000 | Corbo et al. | |
| 6,090,382 A | 7/2000 | Salfeld et al. | |
| 6,165,467 A | 12/2000 | Hagiwara et al. | |
| 6,171,586 B1 | 1/2001 | Lam et al. | |
| 6,177,077 B1 | 1/2001 | Tobinick | |
| 6,214,870 B1 | 4/2001 | McClure et al. | |
| 6,235,281 B1 | 5/2001 | Stenzel et al. | |
| 6,258,562 B1 * | 7/2001 | Salfeld et al. ................ 435/69.6 |
| 6,267,958 B1 | 7/2001 | Andya et al. | |
| 6,270,766 B1 | 8/2001 | Feldman et al. | |
| 6,277,969 B1 * | 8/2001 | Le et al. ....................... 536/23.1 |
| 6,419,944 B2 | 7/2002 | Tobinick | |
| 6,423,321 B2 | 7/2002 | Tobinick et al. | |
| 6,485,725 B1 | 11/2002 | Hirao et al. | |
| 6,485,932 B1 | 11/2002 | McIntosh et al. | |
| 6,509,015 B1 * | 1/2003 | Salfeld et al. .............. 424/142.1 |
| 6,537,549 B2 | 3/2003 | Tobinick | |
| 6,737,405 B2 | 5/2004 | Roemisch et al. | |
| 6,818,613 B2 | 11/2004 | Sharma et al. | |
| 6,875,432 B2 | 4/2005 | Liu et al. | |
| 7,138,118 B2 * | 11/2006 | Le et al. ..................... 424/145.1 |
| 7,141,542 B2 | 11/2006 | Cowan et al. | |
| 7,166,284 B2 * | 1/2007 | Le et al. ..................... 424/145.1 |
| 7,220,409 B2 | 5/2007 | Norman et al. | |
| 7,223,394 B2 | 5/2007 | Salfeld et al. | |
| 7,318,931 B2 | 1/2008 | Okumu et al. | |
| 7,541,031 B2 | 6/2009 | Salfeld et al. | |
| 7,588,761 B2 | 9/2009 | Salfeld et al. | |
| 7,820,169 B2 * | 10/2010 | Heavner et al. ............ 424/145.1 |
| 2001/0021380 A1 | 9/2001 | Pluenneke | |
| 2001/0026801 A1 | 10/2001 | Tobinick | |
| 2003/0012786 A1 | 1/2003 | Teoh et al. | |
| 2003/0124119 A1 | 7/2003 | Yamazaki et al. | |
| 2003/0138417 A1 | 7/2003 | Kaisheva et al. | |
| 2003/0161828 A1 | 8/2003 | Abdelghany et al. | |
| 2003/0190316 A1 | 10/2003 | Kakuta et al. | |
| 2003/0206898 A1 | 11/2003 | Fischkoff et al. | |
| 2003/0235585 A1 | 12/2003 | Fischkoff et al. | |
| 2004/0009172 A1 | 1/2004 | Fischkoff et al. | |

(Continued)

FOREIGN PATENT DOCUMENTS

EP    101 681 B1    3/1984
EP    186 833 B2    7/1986

(Continued)

OTHER PUBLICATIONS

Huang, Pharmacol. Ther., 2000, 86: 201-215.*
Schentrup, PharmaNote, 2003, 18(10): 1-8.*
Stephens et al., Antibody Therapeutics (1997), pp. 317-340, eds. Harris et al., CRC: Boca Raton, Fla.*
den Broeder et al., Rheumatology (Oxford). Jun. 2002;41(6):638-42.*
He et al., Science. Nov. 11, 2005;310(5750):1022-5.*
Atherton et al., Eur J Immunol. Sep. 2000;30(9):2540-7.*
Kurth et al., Am J Hum Genet. Mar. 1991;48(3):613-20.*
Kim et al., Arthritis & Rheumatism vol. 43, No. 3, Mar. 2000, pp. 473-484.*
Malfait et al., Arthritis & Rheumatism, vol. 44, No. 5, May 2001, pp. 1215-1224.*
Douin et al., J Inflamm. 1995-1996;47(1-2):27-38.*
Schattenkirchner et al. (Presented at: The Annual Meeting of the European League Against Rheumatism (EULARO), Prague, Czech Republic, Jun. 2001.*

(Continued)

*Primary Examiner* — Zachary Skelding
(74) *Attorney, Agent, or Firm* — McCarter & English, LLP; Cristin H. Cowles

(57) ABSTRACT

A method of treating TNFα disorders is described, wherein the method comprises administering a low dose amount of a TNFα inhibitor.

12 Claims, 6 Drawing Sheets

(56) References Cited

U.S. PATENT DOCUMENTS

| | | |
|---|---|---|
| 2004/0033228 A1 | 2/2004 | Krause et al. |
| 2004/0038878 A1 | 2/2004 | Tanikawa et al. |
| 2004/0126372 A1 | 7/2004 | Banerjee et al. |
| 2004/0126373 A1 | 7/2004 | Banerjee et al. |
| 2004/0131614 A1 | 7/2004 | Banerjee et al. |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0156835 A1 | 8/2004 | Imoto et al. |
| 2004/0166111 A1 | 8/2004 | Kaymakcalan et al. |
| 2004/0213785 A1 | 10/2004 | Yamazaki et al. |
| 2004/0219142 A1 | 11/2004 | Banerjee et al. |
| 2005/0049402 A1* | 3/2005 | Babcook et al. ......... 530/388.23 |
| 2005/0118163 A1 | 6/2005 | Mizushima et al. |
| 2005/0118167 A1 | 6/2005 | Okada et al. |
| 2005/0214278 A1 | 9/2005 | Kakuta et al. |
| 2006/0009385 A1 | 1/2006 | Hoffman et al. |
| 2006/0083741 A1 | 4/2006 | Hoffman et al. |
| 2006/0127395 A1 | 6/2006 | Arvinte et al. |
| 2006/0153846 A1 | 7/2006 | Krause et al. |
| 2006/0182740 A1 | 8/2006 | Yang et al. |
| 2007/0041905 A1 | 2/2007 | Hoffman et al. |
| 2007/0071747 A1 | 3/2007 | Hoffman et al. |
| 2007/0081996 A1 | 4/2007 | Hoffman et al. |
| 2007/0172897 A1 | 7/2007 | Maksymowych et al. |
| 2007/0202104 A1 | 8/2007 | Banerjee et al. |
| 2007/0243185 A1 | 10/2007 | Gombotz et al. |
| 2007/0292442 A1 | 12/2007 | Wan et al. |
| 2008/0118496 A1 | 5/2008 | Medich et al. |
| 2008/0131374 A1 | 6/2008 | Medich et al. |
| 2008/0166348 A1 | 7/2008 | Kupper et al. |
| 2008/0193466 A1 | 8/2008 | Banerjee et al. |
| 2008/0227136 A1 | 9/2008 | Pla et al. |
| 2008/0311043 A1 | 12/2008 | Hoffman et al. |
| 2009/0017472 A1 | 1/2009 | Stuhlmuller et al. |
| 2009/0028794 A1 | 1/2009 | Medich et al. |
| 2009/0110679 A1 | 4/2009 | Li et al. |
| 2009/0123378 A1 | 5/2009 | Wong et al. |
| 2009/0155205 A1 | 6/2009 | Salfeld et al. |
| 2009/0226530 A1 | 9/2009 | Lassner et al. |
| 2009/0239259 A1 | 9/2009 | Hsieh et al. |
| 2009/0258018 A1 | 10/2009 | Medich et al. |
| 2009/0271164 A1 | 10/2009 | Peng et al. |
| 2009/0291062 A1 | 11/2009 | Fraunhofer et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0016557 A1 | 1/2010 | Salfeld et al. |
| 2010/0021451 A1 | 1/2010 | Wong et al. |

FOREIGN PATENT DOCUMENTS

| | | |
|---|---|---|
| EP | 212 489 B1 | 3/1987 |
| EP | 351 789 A2 | 1/1990 |
| EP | 366 043 A1 | 5/1990 |
| EP | 0486526 A1 | 5/1992 |
| EP | 492 448 A1 | 7/1992 |
| EP | 419251 | 1/1993 |
| EP | 417191 | 10/1993 |
| EP | 614 984 A2 | 9/1994 |
| EP | 659 766 A1 | 6/1995 |
| EP | 1 174 148 A1 | 1/2002 |
| EP | 1 254 666 A1 | 11/2002 |
| EP | 0929578 | 5/2003 |
| GB | 2 279 077 | 12/1994 |
| WO | WO 90/01191 | 2/1990 |
| WO | WO 91/02078 A1 | 2/1991 |
| WO | WO 92/11383 A1 | 7/1992 |
| WO | WO 92/16553 A1 | 10/1992 |
| WO | WO 93/06213 A1 | 4/1993 |
| WO | WO 93/08837 | 5/1993 |
| WO | WO 93/11793 A1 | 6/1993 |
| WO | WO 94/29347 A1 | 12/1994 |
| WO | WO 95/03826 | 2/1995 |
| WO | WO 95/23813 | 9/1995 |
| WO | WO 96/07429 | 3/1996 |
| WO | WO 97/04801 A1 | 2/1997 |
| WO | WO 97/29131 A1 | 8/1997 |
| WO | WO 97/45140 | 12/1997 |
| WO | WO 98/44948 | 10/1998 |
| WO | WO 98/56418 A1 | 12/1998 |
| WO | WO 99/37329 | 7/1999 |
| WO | WO 00/50079 | 8/2000 |
| WO | WO 00/67798 | 11/2000 |
| WO | WO 01/60420 | 8/2001 |
| WO | WO 01/94585 | 12/2001 |
| WO | WO 02/12502 A2 | 2/2002 |
| WO | WO 02/64166 | 8/2002 |
| WO | WO 02/072636 | 9/2002 |
| WO | WO 02/80891 | 10/2002 |
| WO | WO 02/100330 A2 | 12/2002 |
| WO | WO 03/009817 | 2/2003 |
| WO | WO 03/066681 | 8/2003 |
| WO | WO 2004/004633 A2 | 1/2004 |
| WO | WO 2004/007520 | 1/2004 |
| WO | WO 2004/009776 A2 | 1/2004 |
| WO | WO 2004/016286 A2 | 2/2004 |
| WO | WO 2004/037205 A2 | 5/2004 |

OTHER PUBLICATIONS

Shealy et al., mAbs 2:4, 1-12; Jul./Aug. 2010.*
Aulton (Pharmaceutics: The Science of Dosage Form Design, 2nd Ed., pp. 276-288, 2001).*
Weisman et al. (Arthritis Rheum 2000; 43(9) (Suppl.): S391).*
Keane et al. (N Engl J Med 2001;345:1098-104).*
Rowland and Tozer (Lippincott Williams and Wilkins, 1995, pp. 83-105).*
PK Solutions 2.0 Website (Oct. 10, 2002, pp. 1-12).*
Multidose Pharmacokinetics Website Calculator (accessed at http://home.fuse.net/clymer/graphs/pkplot.html on Jun. 27, 2013, pp. 1-4).*
"The Major Components of Blood" Website (May 12, 2001, pp. 1-2).*
Rau et al. (Z Rheumatol 59: Suppl 2, II/90-II/96, 2000).*
Shealy et al. (mAbs 2:4, 1-12; Jul./Aug. 2010).*
Lipsky et al, N Engl J Med 2000;343: 1594-602.*
Barbuto et al. Production of Neutralizing Antibodies to Tumor Necrosis Factor by Human Tumor-Infiltrating B Lymphocytes. Proc. Am. Assoc. Cancer Res. 1993. 34:487, Abstract 2904.
Bendtzen et al. Auto-Antibodies to Il-1β and TNFα in Normal Individuals and in Infectious and Immunoinflammatory Disorders. The Physiological and Pathological Effects of Cytokines. Wiley-Liss, Inc., 1990, pp. 447-452.
Boyle et al. A novel monoclonal human IgM autoantibody which binds recombinant human and mouse tumor necrosis factor-alpha. Cell Immunol. Dec. 1993;152(2):556-68.
Boyle et al. The B5 monoclonal human autoantibody binds to cell surface TNF alpha on human lymphoid cells and cell lines and appears to recognize a novel epitope. Cell lmmunol. Dec. 1993;152(2):569-81.
Chow et al. Effect of Monoclonal Antibody on Human Tumor Necrosis Factor (TNF MAb) on TNFα, IL-1β, and IL-6 Levels in Patients with Sepsis Syndrome. Clinical Research. 1994. 42(2):299A.
Cleland et al. A specific molar ratio of stabilizer to protein is required for storage stability of a lyophilized monoclonal antibody. J Pharm Sci. Mar. 2001;90(3):310-21.
Cox et al. A directory of human germ-line V kappa segments reveals a strong bias in their usage. Eur J Immunol. Apr. 1994;24(4):827-36.
Elliott et al. Treatment of rheumatoid arthritis with chimeric monoclonal antibodies to tumor necrosis factor alpha. Arthritis Rheum. Dec. 1993;36(12):1681-90.
Fomsgaard et al. Auto-antibodies to tumour necrosis factor alpha in healthy humans and patients with inflammatory diseases and gram-negative bacterial infections. Scand J Immunol. Aug. 1989;30(2):219-23.
Griffiths et al. Human anti-self antibodies with high specificity from phage display libraries. EMBO J. Feb. 1993;12(2):725-34.

(56) References Cited

OTHER PUBLICATIONS

Hillgren et al. Protection mechanism of Tween 80 during freeze-thawing of a model protein, LDH. Int J Pharm. Apr. 26, 2002;237(1-2):57-69.

Huse et al. Generation of a large combinatorial library of the immunoglobulin repertoire in phage lambda. Science. Dec. 8, 1989;246(4935):1275-81.

Kempeni et al. Preliminary Results of Early Clinical Trials with the Fully Human Anti-TNFα Monoclonal Antibody D2E7 Annual Rheumatoid Disease. 1999. 58(1):170-172.

Lerner et al. Antibodies without immunization. Science. Nov. 20, 1992;258(5086):1313-4.

Leusch et al. Failure to demonstrate TNF alpha-specific autoantibodies in human sera by ELISA and western blot. J Immunol Methods. May 17, 1991;139(1):145-7.

Lewis et al. J. Cell. Biochem. 1994. 18D:215.

Marks et al. By-passing immunization. Human antibodies from V-gene libraries displayed on phage. J Mol Biol. Dec. 5, 1991;222(3):581-97.

Möller et al. Monoclonal antibodies to human tumor necrosis factor alpha: in vitro and in vivo application. Cytokine. May 1990;2(3):162-9.

Tomlinson et al. The structural repertoire of the human V kappa domain. EMBO J. Sep. 15, 1995;14(18):4628-38.

Tomlinson et al. The repertoire of human germline VH sequences reveals about fifty groups of VH segments with different hypervariable loops. J Mol Biol. Oct. 5, 1992;227(3):776-98.

Tracey et al. Tumor necrosis factor: a pleiotropic cytokine and therapeutic target. Annu Rev Med. 1994;45:491-503.

Winter et al. Humanized antibodies. Immunol Today. Jun. 1993;14(6):243-6.

Baugh, John A. et al, "Mechanisms for modulating TNFα in immune and inflammatory disease," *Current Opinion in Drug Discovery & Development*, vol. 4(5):635-650 (2001).

Elliott, Michael J. et al, "Randomised double-blind comparison of chimeric monoclonal antibody to tumour necrosis factor α (cA2) versus placebo in rheumatoid arthritis," *Lancet*, vol. 344:1105-1110 (1994).

European Search Report for Application No. 03809644.2-2107, dated Mar. 30, 2006.

Rau et al, Experiences with D2E7, Aktuelle Rheumatologie 25(3): 83-88, 2000. [English Translation].

Keffer et al., Transgenic mice expressing human tumour necrosis factor: a predictive genetic model of arthritis. EMBO J. 10(13): 4025-4031, 1991.

Taylor et al., Anti-tumor necrosis factor therpies. Curr. Opin. Rheumatol. 13(3): 164-169, 2001.

Zhou et al., [New drugs for treating Rheumatoid Arthritis] (Chinese). China Pharmacist 2(2): 109, 1999.

Lorenz et al., Perspectives for TNFalpha-targeting therapies. Arthritis Research 4(Suppl 3): S17-S24, 2002.

Lorenz, "Biologocal Agents: a novel approach to the therapy of rheumatoid arthritis", Expert opinion on investigational drugs, Ashley Publications Ltd. London, GB vol. 9, No. 7, 2000, pp. 1479-1490, ISSN: 1354-3784.

Lovell et al., Long-term efficacy and safety of etanercept in children with polyarticular-course juvenile rheumatoid arthritis: interim results from an ongoing multicenter, open-label, extended-treatment trial. Arthritis and Rheumatism 48(1): 218-226, 2003.

Pennington et al., Polyclonal and monoclonal antibody therapy for experimental *Pseudomonas aeruginosa* pneumonia. Infect. Immun. 54: 239-244, 1986.

Shimozato et al., Suppression of tumor necrosis factor alpha production by a human immunoglobulin preparation for intravenous use. Infect. Immun. 58: 1384-1390, 1990.

Sivasai et al., Cytomegalovirus immune globulin intravenous (human) administration. Clin. Exp. Immunol. 119: 559-565, 2000.

Kaymakcalan et al., Comparisons of affinities, avidities, and complement activation of adalimumab, infliximab, and etanercept in binding to soluble and membrane tumor necrosis factor.Clinical Immunology 131: 308-316, 2009.

Rau, Z Rheumatol. vol. 58, suppl 1, p. S51, 1999.

* cited by examiner

LOW DOSE METHODS FOR TREATING DISORDERS IN WHICH TNFα ACTIVITY IS DETRIMENTAL

RELATED APPLICATIONS

This application claims priority to U.S. Provisional Application No. 60/421,262, filed Oct. 24, 2002. This application is related to U.S. Pat. Nos. 6,090,382, 6,258,562, and 6,509,015. This application is also related to U.S. patent application Ser. No. 09/801,185, filed Mar. 7, 2001; and U.S. patent application Ser. No. 10/302,356, filed Nov. 22, 2002. This application is also related to U.S. patent application Ser. No. 10/163,657, filed Jun. 5, 2002, and U.S. patent application Ser. No. 10/133,715, filed Apr. 26, 2002. In addition, this application is related to U.S. application Ser. No. 10/222,140 and U.S. Provisional Application No. 60/403,907, both of which were filed on Aug. 16, 2002. This application is also related to U.S. Provisional Application Ser. No. 60/397,275, filed Jul. 19, 2002; U.S. Provisional Application Ser. No. 60/411,081, filed Sep. 16, 2002; U.S. Provisional Application Ser. No. 60/417,490, filed Oct. 10, 2002; and U.S. Provisional Application Ser. No. 60/455,777, filed Mar. 18, 2003. This application is also related to U.S. patent application Ser. Nos. 10/622,932; 10/623,039; 10/623,076; 10/623,065; 10/622,928; 10/623,075; 10/623,035; 10/622,683; 10/622,205; 10/622,210; 10/622,683, each of which was filed on Jul. 18, 2003. The entire contents of each of these patents and patent applications are hereby incorporated herein by reference.

BACKGROUND OF THE INVENTION

Tumor necrosis factor α (TNFα) is a cytokine produced by numerous cell types, including monocytes and macrophages, that was originally identified based on its capacity to induce the necrosis of certain mouse tumors (see e.g., Old, L. (1985) *Science* 230:630-632). Subsequently, a factor termed cachectin, associated with cachexia, was shown to be the same molecule as TNFα. TNFα has been implicated in mediating shock (see e.g., Beutler, B. and Cerami, A. (1988) *Annu. Rev. Biochem.* 57:505-518; Beutler, B. and Cerami, A. (1989) *Annu. Rev. Immunol.* 7:625-655). Furthermore, TNFα has been implicated in the pathophysiology of a variety of other human diseases and disorders, including sepsis, infections, autoimmune diseases, transplant rejection and graft-versus-host disease (see e.g., Moeller, A., et al. (1990) *Cytokine* 2:162-169; U.S. Pat. No. 5,231,024 to Moeller et al.; European Patent Publication No. 260 610 B1 by Moeller, A., et al., Vasilli, P. (1992) *Annu. Rev. Immunol.* 10:411-452; Tracey, K. J. and Cerami, A. (1994) *Annu. Rev. Med.* 45:491-503).

Because of the harmful role of human TNFα (hTNFα) in a variety of human disorders, therapeutic strategies have been designed to inhibit or counteract hTNFα activity. In particular, antibodies that bind to, and neutralize, hTNFα have been sought as a means to inhibit hTNFα activity. Some of the earliest of such antibodies were mouse monoclonal antibodies (mAbs), secreted by hybridomas prepared from lymphocytes of mice immunized with hTNFα (see e.g., Hahn T; et al., (1985) *Proc Natl Acad Sci USA* 82: 3814-3818; Liang, C-M., et al. (1986) *Biochem. Biophys. Res. Commun.* 137:847-854; Hirai, M., et al. (1987) *J. Immunol. Methods* 96:57-62; Fendly, B. M., et al. (1987) *Hybridoma* 6:359-370; Moeller, A., et al. (1990) *Cytokine* 2:162-169; U.S. Pat. No. 5,231,024 to Moeller et al.; European Patent Publication No. 186 833 B1 by Wallach, D.; European Patent Application Publication No. 218 868 A1 by Old et al.; European Patent Publication No. 260 610 B1 by Moeller, A., et al.). While these mouse anti-hTNFα antibodies often displayed high affinity for hTNFα (e.g., Kd≤$10^{-9}$M) and were able to neutralize hTNFα activity, their use in vivo may be limited by problems associated with administration of mouse antibodies to humans, such as short serum half life, an inability to trigger certain human effector functions and elicitation of an unwanted immune response against the mouse antibody in a human (the "human anti-mouse antibody" (HAMA) reaction).

In an attempt to overcome the problems associated with use of fully-murine antibodies in humans, murine anti-hTNFα antibodies have been genetically engineered to be more "human-like." For example, chimeric antibodies, in which the variable regions of the antibody chains are murine-derived and the constant regions of the antibody chains are human-derived, have been prepared (Knight, D. M, et al. (1993) *Mol. Immunol.* 30:1443-1453; PCT Publication No. WO 92/16553 by Daddona, P. E., et al.). Additionally, humanized antibodies, in which the hypervariable domains of the antibody variable regions are murine-derived but the remainder of the variable regions and the antibody constant regions are human-derived, have also been prepared (PCT Publication No. WO 92/11383 by Adair, J. R., et al.). However, because these chimeric and humanized antibodies still retain some murine sequences, they still may elicit an unwanted immune reaction, the human anti-chimeric antibody (HACA) reaction, especially when administered for prolonged periods, e.g., for chronic indications, such as rheumatoid arthritis (see e.g., Elliott, M. J., et al. (1994) *Lancet* 344:1125-1127; Elliot, M. J., et al. (1994) *Lancet* 344:1105-1110).

A preferred hTNFα inhibitory agent to murine mAbs or derivatives thereof (e.g., chimeric or humanized antibodies) would be an entirely human anti-hTNFα antibody, since such an agent should not elicit the HAMA reaction, even if used for prolonged periods. Human monoclonal autoantibodies against hTNFα have been prepared using human hybridoma techniques (Boyle, P., et al. (1993) *Cell. Immunol.* 152:556-568; Boyle, P., et al. (1993) *Cell. Immunol.* 152:569-581; European Patent Application Publication No. 614 984 A2 by Boyle, et al.). However, these hybridoma-derived monoclonal autoantibodies were reported to have an affinity for hTNFα that was too low to calculate by conventional methods, were unable to bind soluble hTNFα and were unable to neutralize hTNFa-induced cytotoxicity (see Boyle, et al.; supra). Moreover, the success of the human hybridoma technique depends upon the natural presence in human peripheral blood of lymphocytes producing autoantibodies specific for hTNFα. Certain studies have detected serum autoantibodies against hTNFα in human subjects (Fomsgaard, A., et al. (1989) *Scand. J. Immunol.* 30:219-223; Bendtzen, K., et al. (1990) *Prog. Leukocyte Biol.* 10B:447-452), whereas others have not (Leusch, H-G., et al. (1991) *J. Immunol. Methods* 139:145-147).

Alternative to naturally-occurring human anti-hTNFα antibodies would be a recombinant hTNFα antibody. Recombinant human antibodies that bind hTNFα with relatively low affinity (i.e., $K_d \sim 10^{-7}$M) and a fast off rate (i.e., $K_{off} \sim 10^{-2}$ sec$^{-1}$) have been described (Griffiths, A. D., et al. (1993) *EMBO J.* 12:725-734). However, because of their relatively fast dissociation kinetics, these antibodies may not be suitable for therapeutic use. Additionally, a recombinant human anti-hTNFα has been described that does not neutralize hTNFα activity, but rather enhances binding of hTNFα to the surface of cells and enhances internalization of hTNFα (Lidbury, A., et al. (1994) *Biotechnol. Ther.* 5:27-45; PCT Publication No. WO 92/03145 by Aston, R. et al.)

Accordingly, human antibodies, such as recombinant human antibodies, that bind soluble hTNFα with high affinity and slow dissociation kinetics and that have the capacity to treat disorders in which TNFα activity is detrimental, are still needed.

SUMMARY OF THE INVENTION

The invention pertains, at least in part, to methods of administration of low doses of TNFα inhibitors, including, for example, anti-TNFα antibodies, to treat disorders in which TNFα activity is detrimental.

DETAILED DESCRIPTION OF THE INVENTION

Figure 1:
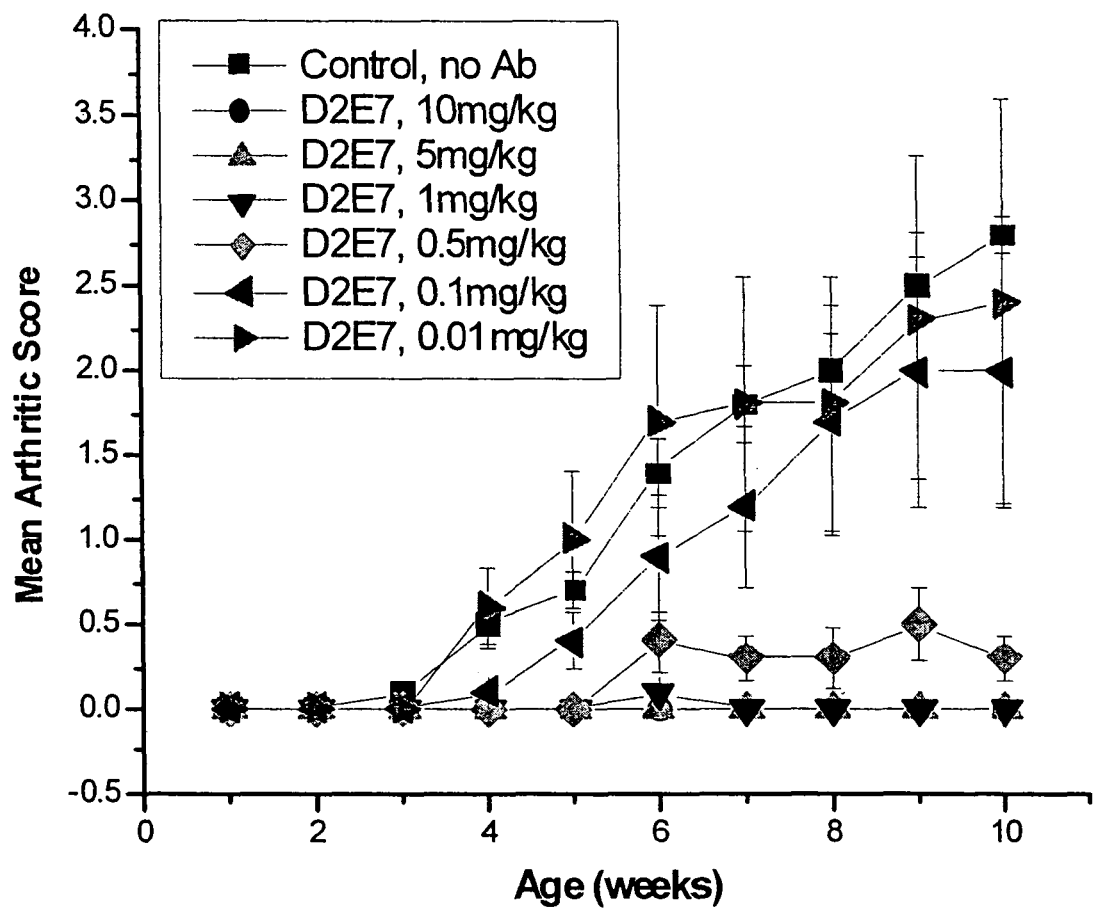
FIG. 1 shows arthritic scores of each mouse in the treatment groups receiving different doses of D2E7. Arthritic scores were recorded weekly starting at 1 week of age. For each treatment group, mean±standard error of arthritis scores are indicated in the graph. The treatment groups were as follows: Control group: 11 female, 9 male mice (n=20); 10 mg/kg dose group: 2 female, 2 male mice (n=4); 5 mg/kg dose group: 6 female, 1 male mice (n=7); 1 mg/kg dose group: 5 female, 3 male mice (n=8); 0.5 mg/kg dose group: 3 female, 2 male mice (n=5); 0.1 mg/kg dose group: 3 female, 3 male mice (n=6); 0.01 mg/kg dose group: 4 female, 2 male mice (n=6).

This invention pertains, at least in part, to low dose methods of treating disorders in which TNFα activity, e.g., human TNFα activity, is detrimental. The methods include administering to the subject an effective amount of a TNFα inhibitor at a low dose, such that the disorder is treated. The invention also pertains to methods wherein the TNFα inhibitor is administered at a low dose in combination with another therapeutic agent and pharmaceutical compositions comprising a TNFα inhibitor, and a pharmaceutically acceptable carrier.

The term "human TNFα" (abbreviated herein as huTNF, hTNFα, or simply hTNF) as used herein, is intended to refer to a human cytokine that exists as a 17 kD secreted form and a 26 kD membrane associated form, the biologically active form of which is composed of a trimer of noncovalently bound 17 kD molecules. The structure of hTNFα is described further in, for example, Pennica, D., et al. (1984) *Nature* 312:724-729; Davis, J. M., et al. (1987) *Biochemistry* 26:1322-1326; and Jones, E. Y., et al. (1989) *Nature* 338:225-228. The term human TNFα is intended to include recombinant human TNFα (rhTNFα), which can be prepared by standard recombinant expression methods or purchased commercially (R & D Systems, Catalog No. 210-TA, Minneapolis, Minn.).

The term "TNFα inhibitor" includes agents which inhibit TNFα. Examples of TNFα inhibitors include etanercept (Enbrel® (etanercept), Immunex), infliximab (REMICADE® (infliximab), Johnson and Johnson), human anti-TNF monoclonal antibody (D2E7, Knoll Pharmaceuticals), CDP 571 (Celltech), and CDP 870 (Celltech) and other compounds which inhibit TNFα activity, such that when administered to a subject suffering from or at risk of suffering from a disorder in which TNFα activity is detrimental, the disorder is treated. The term also includes each of the anti-TNFα human antibodies and antibody portions described herein as well as those described in U.S. Pat. Nos. 6,090,382 and 6,258,562 B1, and in U.S. patent application Ser. Nos. 09/540,018, and 09/801,185.

The term "antibody", as used herein, is intended to refer to immunoglobulin molecules comprised of four polypeptide chains, two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The antibodies of the invention are described in further detail in U.S. Pat. Nos. 6,090,382 and 6,258,562 B1, and in U.S. patent application Ser. Nos. 09/540,018, and 09/801,185, each of which is incorporated herein by reference in its entirety.

The term "antigen-binding portion" of an antibody (or simply "antibody portion"), as used herein, refers to one or more fragments of an antibody that retain the ability to specifically bind to an antigen (e.g., hTNFα). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123). The antibody portions of the invention are described in further detail in U.S. Pat. Nos. 6,090,382 and 6,258,562 B1, and in U.S. patent application Ser. Nos. 09/540,018, and 09/801,185, each of which is incorporated herein by reference in its entirety.

In one embodiment of the invention, D2E7 antibodies and antibody portions, D2E7-related antibodies and antibody portions, and other human antibodies and antibody portions with equivalent properties to D2E7, such as high affinity binding to hTNFα with low dissociation kinetics and high neutralizing capacity are used in low dose methods of treating disorders associated with detrimental TNF activity. In another one embodiment, a human antibody, or an antigen-binding portion thereof, that dissociates from human TNFα with a $K_d$ of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an $IC_{50}$ of $1\times10^{-7}$ M or less is used in low dose methods of treating disorders associated with detrimental TNF activity. In a further embodiment, an isolated human antibody, or antigen-binding portion thereof, dissociates from human TNFα with a $K_{off}$ of $5\times10^{-4}$ s$^{-1}$ or less, or even more preferably, with a $K_{off}$ of $1\times10^{-4}$ s$^{-1}$ or less is used in low dose methods of treating disorders associated with detrimental TNF activity. More preferably, the isolated human antibody, or antigen-binding portion thereof, neutralizes human TNFα cytotoxicity in a standard in vitro L929 assay with an $IC_{50}$ of $1\times10^{-8}$ M or less, even more preferably with an $IC_{50}$ of $1\times10^{-9}$ M or less and still more preferably with an $IC_{50}$ of $5\times10^{-10}$ M or less.

The term "low dose" or "low dosage" as used herein, refers to an amount of TNFα inhibitor which is administered to a subject, wherein the amount is substantially lower than that ordinarily employed. A "low dose therapy" includes a treatment regimen which is based on administering a low dose of a TNFα inhibitor. In one embodiment of the invention, a low dose of D2E7 is administered to a subject to treat TNFα-associated disorders which are detrimental. In a further embodiment, a low dose of TNFα inhibitor, including, for example, D2E7, is used to treat rheumatoid arthritis and symptoms associated with the disease. For example, symptoms which can be treated using low dose therapy of D2E7 include bone erosion, cartilage erosion, inflammation, and vascularity. Low doses of a TNFα inhibitor are advantageous for a number of reasons, including the reduction in the frequency and severity of side effects which may be associated with the normal prescribed dose of TNFα inhibitor.

I. Uses of TNFα Inhibitors of the Invention

In an embodiment, the invention provides a low dose method for inhibiting TNFα activity in a subject suffering from a disorder in which TNFα activity is detrimental. TNFα has been implicated in the pathophysiology of a wide variety of disorders (see e.g., Moeller, A., et al. (1990) *Cytokine* 2:162-169; U.S. Pat. No. 5,231,024 to Moeller et al.; European Patent Publication No. 260 610 B1 by Moeller, A). The invention provides methods for inhibiting TNFα activity in a subject suffering from such a disorder, which method comprises administering to the subject low dose of an antibody, antibody portion, or other TNFα inhibitor of the invention such that TNFα activity in the subject is inhibited. Preferably, the TNFα is human TNFα and the subject is a human subject. Alternatively, the subject can be a mammal expressing a TNFα with which an antibody of the invention cross-reacts. An antibody of the invention can be administered to a human subject for therapeutic purposes in low doses (discussed further below). Moreover, a low dose of an antibody of the invention can be administered to a non-human mammal expressing a TNFα with which the antibody cross-reacts (e.g., a primate, pig or mouse) for veterinary purposes or as an animal model of human disease. Regarding the latter, such animal models may be useful for evaluating the therapeutic efficacy of antibodies of the invention (e.g., testing of dosages and time courses of administration).

As used herein, the term "a disorder in which TNFα activity is detrimental" is intended to include diseases and other disorders in which the presence of TNFα in a subject suffering from the disorder has been shown to be or is suspected of being either responsible for the pathophysiology of the disorder or a factor that contributes to a worsening of the disorder. For the purposes of the invention, treating a disorder in which TNFα activity is detrimental includes, but is not limited to, alleviating symptoms associated with said disorder. Accordingly, a disorder in which TNFα activity is detrimental is a disorder in which inhibition of TNFα activity is expected to alleviate the symptoms and/or progression of the disorder. Such disorders may be evidenced, for example, by an increase in the concentration of TNFα in a biological fluid of a subject suffering from the disorder (e.g., an increase in the concentration of TNFα in serum, plasma, synovial fluid, etc. of the subject), which can be detected, for example, using an anti-TNFα antibody as described above. There are numerous examples of disorders in which TNFα activity is detrimental. The use of a low dose of antibodies, antibody portions, and other TNFα inhibitors of the invention in the treatment of specific disorders are discussed further below. In certain embodiments, a low dose of the antibody, antibody portion, or other TNFα inhibitor of the invention is administered to the subject in combination with another therapeutic agent, as described below.

A. Sepsis

Tumor necrosis factor has an established role in the pathophysiology of sepsis, with biological effects that include hypotension, myocardial suppression, vascular leakage syndrome, organ necrosis, stimulation of the release of toxic secondary mediators and activation of the clotting cascade (see e.g., Moeller, A., et al. (1990) *Cytokine* 2:162-169; U.S. Pat. No. 5,231,024 to Moeller et al.; European Patent Publication No. 260 610 B1 by Moeller, A.; Tracey, K. J. and Cerami, A. (1994) *Annu. Rev. Med.* 45:491-503; Russell, D. and Thompson, R. C. (1993) *Curr. Opin. Biotech.* 4:714-721). Accordingly, the human antibodies, antibody portions, and other TNFα inhibitors of the invention can be used to treat sepsis in any of its clinical settings, including septic shock, endotoxic shock, gram negative sepsis and toxic shock syndrome.

Furthermore, to treat sepsis, an anti-hTNFα antibody, antibody portion, or other TNFα inhibitor of the invention can be coadministered with one or more additional therapeutic agents that may further alleviate sepsis, such as an interleukin-1 inhibitor (such as those described in PCT Publication Nos. WO 92/16221 and WO 92/17583), the cytokine interleukin-6 (see e.g., PCT Publication No. WO 93/11793) or an antagonist of platelet activating factor (see e.g., European Patent Application Publication No. EP 374 510). Other combination therapies for the treatment of sepsis are discussed further in subsection II.

Additionally, in an embodiment, an anti-TNFα antibody, antibody portion, or other TNFα inhibitor of the invention is administered to a human subject within a subgroup of sepsis patients having a serum or plasma concentration of IL-6 above 500 pg/ml, and more preferably 1000 pg/ml, at the time of treatment (see PCT Publication No. WO 95/20978 by Daum, L., et al.).

B. Autoimmune Diseases

Tumor necrosis factor has been implicated in playing a role in the pathophysiology of a variety of autoimmune diseases. For example, TNFα has been implicated in activating tissue inflammation and causing joint destruction in rheumatoid arthritis (see e.g., Moeller, A., et al. (1990) *Cytokine* 2:162-169; U.S. Pat. No. 5,231,024 to Moeller et al.; European Patent Publication No. 260 610 B1 by Moeller, A.; Tracey and Cerami, supra; Arend, W. P. and Dayer, J-M. (1995) *Arth. Rheum.* 38:151-160; Fava, R. A., et al. (1993) *Clin. Exp. Immunol.* 94:261-266). TNFα also has been implicated in promoting the death of islet cells and in mediating insulin resistance in diabetes (see e.g., Tracey and Cerami, supra; PCT Publication No. WO 94/08609). TNFα also has been implicated in mediating cytotoxicity to oligodendrocytes and induction of inflammatory plaques in multiple sclerosis (see e.g., Tracey and Cerami, supra). Chimeric and humanized murine anti-hTNFα antibodies have undergone clinical testing for treatment of rheumatoid arthritis (see e.g., Elliott, M. J., et al. (1994) *Lancet* 344:1125-1127; Elliot, M. J., et al. (1994) *Lancet* 344:1105-1110; Rankin, E. C., et al. (1995) *Br. J. Rheumatol.* 34:334-342).

In one embodiment of the invention, low doses of anti-TNFα antibodies of the invention can be used to treat rheumatoid arthritis. Low doses of anti-TNFα antibodies can be used to treat rheumatoid arthritis by alleviating symptoms associated with said disorder. Examples of symptoms or signs commonly associated with rheumatoid arthritis include, but are not limited to, bone erosion in the joints, cartilage erosion in the joints, inflammation in the joints, vascularity in the joints, and combinations thereof. Other examples of symptoms associated with rheumatoid arthritis include weight gain, joint distortion, swelling of the joints, joint deformation, ankylosis on felxion, severely impaired movement, and combinations thereof.

The human antibodies, antibody portions, and other TNFα inhibitors of the invention can be used to treat autoimmune diseases, in particular those associated with inflammation, including rheumatoid arthritis, rheumatoid spondylitis, osteoarthritis and gouty arthritis, allergy, multiple sclerosis, autoimmune diabetes, autoimmune uveitis and nephrotic syndrome. Typically, the antibody, antibody portion, or other TNFα inhibitor is administered systemically, although for certain disorders, local administration of the antibody, antibody portion, or other TNFα inhibitor at a site of inflammation may be beneficial (e.g., local administration in the joints in rheumatoid arthritis or topical application to diabetic ulcers, alone or in combination with a cyclohexane-ylidene derivative as described in PCT Publication No. WO 93/19751). An antibody, antibody portion, or other TNFα inhibitor of the invention also can be administered with one or more additional therapeutic agents useful in the treatment of autoimmune diseases, as discussed further in subsection II.

The antibodies, antibody portions, and other TNFα inhibitors of the invention, also can be used to treat multisystem autoimmune diseases, including sarcoidosis and Behcet's disease.

C. Infectious Diseases

Tumor necrosis factor has been implicated in mediating biological effects observed in a variety of infectious diseases. For example, TNFα has been implicated in mediating brain inflammation and capillary thrombosis and infarction in malaria. TNFα also has been implicated in mediating brain inflammation, inducing breakdown of the blood-brain barrier, triggering septic shock syndrome and activating venous infarction in meningitis. TNFα also has been implicated in inducing cachexia, stimulating viral proliferation and mediating central nervous system injury in acquired immune deficiency syndrome (AIDS). Accordingly, the antibodies, antibody portions, and other TNFα inhibitors of the invention, can be used in the treatment of infectious diseases, including bacterial meningitis (see e.g., European Patent Application Publication No. EP 585 705), cerebral malaria, AIDS and AIDS-related complex (ARC) (see e.g., European Patent Application Publication No. EP 230 574), as well as cytomegalovirus infection secondary to transplantation (see e.g., Fietze, E., et al. (1994) *Transplantation* 58:675-680). The antibodies, antibody portions, or other TNFα inhibitors of the invention, also can be used to alleviate symptoms associated with infectious diseases, including fever and myalgias due to infection (such as influenza) and cachexia secondary to infection (e.g., secondary to AIDS or ARC).

D. Transplantation

Tumor necrosis factor has been implicated as a key mediator of allograft rejection and graft versus host disease (GVHD) and in mediating an adverse reaction that has been observed when the rat antibody OKT3, directed against the T cell receptor CD3 complex, is used to inhibit rejection of renal transplants (see e.g., Eason, J. D., et al. (1995) *Transplantation* 59:300-305; Suthanthiran, M. and Strom, T. B. (1994) *New Engl. J. Med.* 331:365-375). Accordingly, the antibodies, antibody portions, and other TNFα inhibitors of the invention, can be used to inhibit transplant rejection, including rejections of allografts and xenografts and to inhibit GVHD. Although the antibody, antibody portion, or other TNFα inhibitor may be used alone, more preferably it is used in combination with one or more other agents that inhibit the immune response against the allograft or inhibit GVHD. For example, in one embodiment, an antibody, antibody portion, or other TNFα inhibitor of the invention is used in combination with OKT3 to inhibit OKT3-induced reactions. In another embodiment, an antibody, antibody portion, other TNFα inhibitor of the invention is used in combination with one or more antibodies directed at other targets involved in regulating immune responses, such as the cell surface molecules CD25 (interleukin-2 receptor-α), CD11a (LFA-1), CD54 (ICAM-1), CD4, CD45, CD28/CTLA4, CD80 (B7-1) and/or CD86 (B7-2). In yet another embodiment, an antibody, antibody portion, or other TNFα inhibitor of the invention is used in combination with one or more general immunosuppressive agents, such as cyclosporin A or FK506.

E. Malignancy

Tumor necrosis factor has been implicated in inducing cachexia, stimulating tumor growth, enhancing metastatic potential and mediating cytotoxicity in malignancies. Accordingly, the antibodies, and antibody portions, of the invention, can be used in the treatment of malignancies, to inhibit tumor growth or metastasis and/or to alleviate cachexia secondary to malignancy. The antibody, antibody portion, other TNFα inhibitor may be administered systemically or locally to the tumor site.

The antibodies, antibody portions, and other TNFα inhibitors of the invention, also can be used to treat malignant disorders associated with solid tumors and/or leukemias and lymphomas. Examples of solid tumors which can be treated with the antibodies of the invention include, but are not limited to, ovarian cancer and colorectal cancer. Examples of leukemias and lymphomas which can be treated with the antibodies of the invention include, but are not limited to, myelo dysplastic syndrome and multiple myeloma.

F. Pulmonary Disorders

Tumor necrosis factor has been implicated in the pathophysiology of adult respiratory distress syndrome (ARDS), including stimulating leukocyte-endothelial activation, directing cytotoxicity to pneumocytes and inducing vascular leakage syndrome. Accordingly, the antibodies, antibody portions, and other TNFα inhibitors of the invention, can be used to treat various pulmonary disorders, including adult respiratory distress syndrome (see e.g., PCT Publication No. WO 91/04054), shock lung, chronic pulmonary inflammatory disease, pulmonary sarcoidosis, pulmonary fibrosis, asilicosis, asthma, chronic obstructive pulmonary disease (COPD), and idiopathic pulmonary fibrosis (UIP or interstitial lung disease). The antibody, antibody portion, or other TNFα inhibitor may be administered systemically or locally to the lung surface, for example as an aerosol. An antibody, antibody portion, or other TNFα inhibitor of the invention also can be administered with one or more additional therapeutic agents useful in the treatment of pulmonary disorders, as discussed further in subsection II.

G. Intestinal Disorders

Tumor necrosis factor has been implicated in the pathophysiology of inflammatory bowel disorders (see e.g., Tracy, K. J., et al. (1986) *Science* 234:470-474; Sun, X-M., et al. (1988) *J. Clin. Invest.* 81:1328-1331; MacDonald, T. T., et al. (1990) *Clin. Exp. Immunol.* 81:301-305). Chimeric murine anti-hTNFα antibodies have undergone clinical testing for treatment of Crohn's disease (van Dullemen, H. M., et al. (1995) *Gastroenterology* 109:129-135). The human antibodies, antibody portions, and other TNFα inhibitors of the invention, also can be used to treat intestinal disorders, such as idiopathic inflammatory bowel disease, which includes two syndromes, Crohn's disease and ulcerative colitis. An antibody, antibody portion, and other TNFα inhibitors of the invention also can be administered with one or more additional therapeutic agents useful in the treatment of intestinal disorders, as discussed further in subsection II.

H. Cardiac Disorders

The antibodies, antibody portions, and other TNFα inhibitors of the invention, also can be used to treat various cardiac disorders, including ischemia of the heart (see e.g., European Patent Application Publication No. EP 453 898) and heart insufficiency (weakness of the heart muscle) (see e.g., PCT Publication No. WO 94/20139).

The antibodies, antibody portions, and other TNFα inhibitors of the invention, also can be used to treat cardiovascular disorders including, but not limited to, chronic artherosclerosis, cardiomyopathy, congestive heart failure, and rheumatic heart disease.

I. Neurological Disorders

The antibodies, antibody portions, and other TNFα inhibitors of the invention, can be used to treat neurological disorders, including, for example, Alzheimer's, Sciatica, peripheral neuropathy, and neuropathic pain.

J. Metabolic Disease

Tumor necrosis factor has been implicated in mediating biological effects observed in a variety of metabolic diseases. For example, the antibodies, antibody portions, and other TNFα inhibitors of the invention can be used to treat cachexia.

Tumor necrosis factor has also been implicated in mediating the biological effects observed in diabetes and complications associated with diabetes. Diabetic conditions include, but are not limited to, type 1 diabetes mellitus, type 2 diabetes mellitus, diabetic vasculopathy, and neuropathic pain.

K. Liver Disease

Tumor necrosis factor has been implicated in mediating biological effects observed in a variety of liver diseases. The antibodies, antibody portions, and other TNFα inhibitors of the invention, can be used to treat liver diseases, including, for example, hepatitis C, schlerosing cholangitis, autoimmune hepatitis, and chronic liver failure.

L. Kidney Disease

Tumor necrosis factor has been implicated in mediating biological effects observed in a variety of kidney diseases. The antibodies, antibody portions, and other TNFα inhibitors of the invention, can be used to treat kidney diseases, including, for example progressive renal failure. The antibodies of the invention can also be used to treat glomerulonephrities, including, for example, post-streptococcal glomerulonephritis and IgA nephropathy.

M. Inflammatory Disease

1. Inflammatory Joint Disease

The antibodies, antibody portions, and other TNFα inhibitors of the invention, also can be used to treat inflammatory joint disease, including, for example, Adult Still's disease, juvenile rheumatoid arthritis, Still's disease, Reiter's syndrome, and spondyloarthropathies. The antibodies of the invention can also be used to treat spondyloarthropathies. Examples of spondyloarthropathies include, for example, ankylosing spondylitis, psoriatic arthritis, and undifferentiated spondyloarthropathies.

2. Inflammatory Connective Tissue Disease

The antibodies, antibody portions, and other TNFα inhibitors of the invention, also can be used to treat inflammatory connective tissue diseases, including, for example, dermato/polymyositis, scleroderma, mixed connective tissue disorder, relapsing polychondritis, and vascultides. Examples of vascultides include Wegener's granulomatosis, temporal arteritis (GCA) and polymyalgia rheumatica, Takayasu's arteritis, polyarteritis nodosa, microscopic polyangiitis, Churg-Strauss syndrome, and Kawasaki syndrome.

3. Inflammatory Skin and Mucosal Diseases

The antibodies, antibody portions, and other TNFα inhibitors of the invention, also can be used to treat inflammatory skin and mucosal diseases, including, for example, psoriasis, pemphigus vulgaris, Jarisch-Herxheimer reaction, pyoderma gangerenosum, and drug reactions such as erythema multiforme and Stevens Johnson syndrome.

4. Inflammatory Diseases of Sensory Organs

The antibodies, antibody portions, and other TNFα inhibitors of the invention, can be used to treat inflammatory diseases of the sensory organs, including uveitis and autoimmune hearing loss. The antibodies of the invention can also be used to treat inflammatory diseases associated with the ear, including chronic otitis media with or without cholesteatoma, chronic ear inflammation, and pediatric ear inflammation. Clinical studies have shown that cytokines, including TNFα, are upregulated in patients with chronic otitis media with cholesteatoma (Yetiser et al. (2002) *Otology and Neurotology* 23: 647-652). The antibodies of the invention can be used to treat inflammation and cholesteatoma associated with otitis media.

5. Inflammatory/Autoimmunne Diseases of Other Organ Systems

The antibodies, antibody portions, and other TNFα inhibitors of the invention, can be used to treat inflammatory/autoimmune diseases of other organ systems, including, for example, familial periodic fevers, prostatitis, Felty's syndrome, Sjogren's syndrome, acute pancreatitis, chronic pancreatitis, and orchitis.

N. Degenerative Bone and Joint Disease

The antibodies, antibody portions, and other TNFα inhibitors of the invention, can be used to treat various disorders associated with degenerative bone and joint disease, including, for example, pseudogout, ostoarthritis, periodontal disease, and loosening of prostheses, e.g. artificial hips (metallic head of femur, etc.) or osteolysis.

O. Reperfusion Injury

The antibodies, antibody portions, and other TNFα inhibitors of the invention, can be used to treat various disorders associated with reperfusion injury, including, for example, stroke and myocardial infarction.

P. Others

The antibodies, and antibody portions, of the invention, also can be used to treat various other disorders in which TNFα activity is detrimental. Examples of other diseases and disorders in which TNFα activity has been implicated in the pathophysiology, and thus which can be treated using an antibody, antibody portion, or other TNFα inhibitor of the invention, include inflammatory bone disorders and bone resorption disease (see e.g., Bertolini, D. R., et al. (1986) *Nature* 319:516-518; Konig, A., et al. (1988) *J. Bone Miner. Res.* 3:621-627; Lerner, U. H. and Ohlin, A. (1993) *J. Bone Miner. Res.* 8:147-155; and Shankar, G. and Stern, P. H. (1993) *Bone* 14:871-876), hepatitis, including alcoholic hepatitis (see e.g., McClain, C. J. and Cohen, D. A. (1989) *Hepatology* 9:349-351; Felver, M. E., et al. (1990) *Alcohol. Clin. Exp. Res.* 14:255-259; and Hansen, J., et al. (1994) *Hepatology* 20:461-474), viral hepatitis (Sheron, N., et al. (1991) *J. Hepatol.* 12:241-245; and Hussain, M. J., et al. (1994) *J. Clin. Pathol.* 47:1112-1115), and fulminant hepatitis; coagulation disturbances (see e.g., van der Poll, T., et al. (1990) *N. Engl. J. Med.* 322:1622-1627; and van der Poll, T., et al. (1991) *Prog. Clin. Biol. Res.* 367:55-60), burns (see e.g., Giroir, B. P., et al. (1994) *Am. J. Physiol.* 267:H118-124; and Liu, X. S., et al. (1994) *Burns* 20:40-44), reperfusion injury (see e.g., Scales, W. E., et al. (1994) *Am. J. Physiol.* 267: G1122-1127; Serrick, C., et al. (1994) *Transplantation* 58:1158-1162; and Yao, Y. M., et al. (1995) *Resuscitation* 29:157-168), keloid formation (see e.g., McCauley, R. L., et al. (1992) *J. Clin. Immunol.* 12:300-308), scar tissue formation; pyrexia; periodontal disease; obesity and radiation toxicity.

Other disorders in which TNFα activity is detrimental include, but are not limited to, hepatotoxicity, adult Still's disease, Alzheimer's disease, ankylosing spondylitis, asthma, cancer and cachexia, atherosclerosis, chronic atherosclerosis, chronic fatigue syndrome, liver failure, chronic liver failure, obstructive pulmonary disease, chronic obstructive pulmonary disease, congestive heart failure, dermatopolymyositis, diabetic macrovasculopathy, endometriosis, familial periodic fevers, fibrosis, hemodialysis, Jarisch-Herxheimer reaction, juvenile RA, Kawasaki syndrome, myelo dysplastic syndrome, myocardial infarction, panciaticular vulgaris, periodontal disease, peripheral neuropathy, polyarticular, polymyositis, progressive renal failure, psoriasis, psoriatic arthritis, Reiter's syndrome, sarcoidosis, scleroderma, spondyloarthropathies, Still's disease, stroke, therapy associated syndrome, therapy induced inflammatory syndrome, inflammatory syndrome following IL-2 administration, thoracoabdominal aortic aneurysm repair (TAAA), Vasulo-Behcet's disease, Yellow Fever vaccination, type 1 diabetes mellitus, type 2 diabetes mellitus, neuropathic pain, sciatica, cerebral edema, edema in and/or around the spinal cord, vasculitide, Wegener's granulomatosis, temporal arteritis, polymyalgia rheumatica, Takayasu's arteritis, polyarteritis nodosa, microscopic polyangiitis, Churg-Strauss syndrome, Felty's syndrome, Sjogren's syndrome, mixed connective tissue disorder, relapsing polychondritis, pseudogout, loosening of prostheses, autoimmune hepatitis, sclerosing cholangitis, acute pancreatitis, chronic pancreatitis, glomerulonephritides, post-streptococcal glomerulonephritis or IgA nephropathy, rheumatic heart disease, cardiomyopathy, orchitis, pyoderma gangerenosum, multiple myeloma, TNF receptor associated periodic syndrome [TRAPS], atherosclerosis, steroid dependent giant cell arteritismyostitis, uveitis, and drug reactions.

II. Pharmaceutical Compositions and Pharmaceutical Administration

The antibodies, antibody-portions, and other TNFα inhibitors of the invention can be incorporated into pharmaceutical compositions suitable for low dose administration to a subject. Typically, the pharmaceutical composition comprises an antibody, antibody portion, or other TNFα inhibitor of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody, antibody portion, or other TNFα inhibitor.

The compositions of this invention may be in a variety of forms suitable for low dose administration. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies or other TNFα inhibitors. The preferred mode of administration is parenteral (e.g., intravenous, subcutaneous, intraperitoneal, intramuscular). In a preferred embodiment, a low dose of the antibody or other TNFα inhibitor is administered by intravenous infusion or injection. In another preferred embodiment, a low dose of the antibody or other TNFα inhibitor is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating a low dose of the active compound (i.e., antibody, antibody portion, or other TNFα inhibitor) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The invention also pertains to packaged pharmaceutical compositions which comprise a low dose of a TNFα inhibitor of the invention and instructions for using the inhibitor to treat a particular disorder in which TNFα activity is detrimental, as described above.

The pharmaceutical compositions of the invention may include a "therapeutically effective amount" or a "prophylactically effective amount" of an antibody or antibody portion of the invention. A "therapeutically effective amount" is any amount which is determined to be required to eliminate said disorder or to reduce and/or alleviate the symptoms of said disorder. In a preferred embodiment of the invention, a "therapeutically effective amount" refers to an amount which is effective, at low doses and for periods of time necessary, to achieve the desired therapeutic result. A therapeutically effective amount of the antibody, antibody portion, or other TNFα inhibitor may vary according to factors such as the disease state, age, sex, and weight of the individual, and the ability of the antibody, antibody portion, other TNFα inhibitor to elicit a desired response in the individual. A therapeutically effective amount is also one in which any toxic or detrimental effects of the antibody, antibody portion, or other TNFα inhibitor are outweighed by the therapeutically beneficial effects.

Dosage regimens may be adjusted to provide the optimum desired response (e.g., a therapeutic or prophylactic response). For example, a single bolus may be administered, several divided low doses may be administered over time or the low dose may be proportionally reduced or increased as indicated by the exigencies of the therapeutic situation. It is especially advantageous to formulate parenteral compositions in low dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antibody, antibody portion, or other TNFα inhibitor of the invention is 0.01-2.0 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In one embodiment of the invention, the therapeutically effective amount of an anti-TNFα antibody is a low dose. In one embodiment, the low dose of the antibody administered to a subject suffering from a disorder in which TNFα is detrimental, is between about 0.01-2.0 mg/kg, about 0.06-1.9 mg/kg, about 0.11-1.8 mg/kg, about 0.16-1.7 mg/kg, about 0.21-1.6 mg/kg, about 0.26-1.5 mg/kg, about 0.31-1.4 mg/kg, about 0.36-1.3 mg/kg, about 0.41-1.2 mg/kg, about 0.46-1.1 mg/kg, about 0.51-1.0 mg/kg, about 0.56-0.9 mg/kg, about 0.61-0.8 mg/kg, and about 0.66-0.7 mg/kg. In a preferred embodiment, the antibody is D2E7. Ranges intermediate to the above recited dosages, e.g. about 0.17-1.65 mg/kg are also intended to be part of this invention. For example, ranges of values using a combination of any of the above recited values as upper and/or lower limits are intended to be included.

A low dose of the antibodies, antibody-portions, and other TNFα inhibitors of the present invention can be administered by a variety of methods known in the art, although for many therapeutic applications, the preferred route/mode of administration is intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

In certain embodiments, a low dose of an antibody, antibody portion, or other TNFα inhibitor of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a low dose of the compound of the invention by other than parenteral administration, it may be necessary to coat the compound with, or co-administer the compound with, a material to prevent its inactivation.

Supplementary active compounds can also be incorporated into the compositions. In certain embodiments, a low dose of an antibody or antibody portion of the invention is coformulated with and/or coadministered with one or more additional therapeutic agents that are useful for treating disorders in which TNFα activity is detrimental. For example, a low dose of an anti-hTNFα antibody, antibody portion, or other TNFα inhibitor of the invention may be coformulated and/or coadministered with one or more additional antibodies that bind other targets (e.g., antibodies that bind other cytokines or that bind cell surface molecules), one or more cytokines, soluble TNFα receptor (see e.g., PCT Publication No. WO 94/06476) and/or one or more chemical agents that inhibit hTNFα production or activity (such as cyclohexane-ylidene derivatives as described in PCT Publication No. WO 93/19751). Furthermore, a low dose of one or more antibodies or other TNFα inhibitors of the invention may be used in combination with two or more of the foregoing therapeutic agents. Such combination therapies may advantageously utilize even lower dosages of the administered therapeutic agents, thus avoiding possible toxicities or complications associated with the various monotherapies.

III. Other Therapeutic Agents

The language "in combination with" a therapeutic agent includes co-administration of a low dose of the antibody, antibody portion, or other TNFα inhibitor of the invention with a therapeutic agent, administration of a low dose of the antibody, antibody portion, or other TNFα inhibitor of the invention first, followed by the therapeutic agent and administration of the therapeutic agent first, followed by the low dose of the antibody, antibody portion, or other TNFα inhibitor of the invention. Specific therapeutic agent(s) are generally selected based on the particular disorder being treated, as discussed below.

Nonlimiting examples of therapeutic agents for rheumatoid arthritis with which a low dose of an antibody, antibody portion, or other TNFα inhibitor of the invention can be combined include the following: non-steroidal anti-inflammatory drug(s) (NSAIDs); cytokine suppressive anti-inflammatory drug(s) (CSAIDs); CDP-571/BAY-10-3356 (humanized anti-TNFα antibody; Celltech/Bayer); cA2 (chimeric anti-TNFα antibody; Centocor); 75 kdTNFR-IgG (75 kD TNF receptor-IgG fusion protein; Immunex; see e.g., Arthritis & Rheumatism (1994) Vol. 37, S295; J. Invest. Med. (1996) Vol. 44, 235A); 55 kdTNFR-IgG (55 kD TNF receptor-IgG fusion protein; Hoffmann-LaRoche); IDEC-CE9.1/SB 210396 (non-depleting primatized anti-CD4 antibody; IDEC/SmithKline; see e.g., Arthritis & Rheumatism (1995) Vol. 38, S185); DAB 486-IL-2 and/or DAB 389-IL-2 (IL-2 fusion proteins; Seragen; see e.g., Arthritis & Rheumatism (1993) Vol. 36, 1223); Anti-Tac (humanized anti-IL-2Rα; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-1RA (IL-1 receptor antagonist; Synergen/Amgen); TNF-bp/s-TNFR (soluble TNF binding protein; see e.g., Arthritis & Rheumatism (1996) Vol. 39, No. 9 (supplement), S284; Amer. J. Physiol.—Heart and Circulatory Physiology (1995) Vol. 268, pp. 37-42); R973401 (phosphodiesterase Type IV inhibitor; see e.g., Arthritis & Rheumatism (1996) Vol. 39 No. 9 (supplement), S282); MK-966 (COX-2 Inhibitor; see e.g., Arthritis & Rheumatism (1996) Vol. 39, No. 9 (supplement), S81); Iloprost (see e.g., Arthritis & Rheumatism (1996) Vol. 39, No. 9 (supplement), S82); methotrexate; thalidomide (see e.g., Arthritis & Rheumatism (1996) Vol. 39, No. 9 (supplement), S282) and thalidomide-related drugs (e.g., Celgen); leflunomide (anti-inflammatory and cytokine inhibitor; see e.g., Arthritis & Rheumatism (1996) Vol. 39, No. 9 (supplement), S131; Inflammation Research (1996) Vol. 45 pp. 103-107); tranexamic acid (inhibitor of plasminogen activation; see e.g., Arthritis & Rheumatism (1996) Vol. 39, No. 9 (supplement), S284); T-614 (cytokine inhibitor; see e.g., Arthritis & Rheumatism (1996) Vol. 39, No. 9 (supplement), S282); prostaglandin E1 (see e.g., Arthritis & Rheumatism (1996) Vol. 39, No. 9 (supplement), S282); Tenidap (non-steroidal anti-inflammatory drug; see e.g., Arthritis & Rheumatism (1996) Vol. 39 No. 9 (supplement), S280); Naproxen (non-steroidal anti-inflammatory drug; see e.g., Neuro Report (1996) Vol. 39, pp. 1209-1213); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine (see e.g., Arthritis & Rheumatism (1996) Vol. 39, No. 9 (supplement), S281); Azathioprine (see e.g., Arthritis & Rheumatism (1996) Vol. 39, No. 9 (supplement), S281); ICE inhibitor (inhibitor of the enzyme interleukin-1β converting enzyme); zap-70 and/or lck inhibitor (inhibitor of the tyrosine kinase zap-70 or lck); VEGF inhibitor and/or VEGF-R inhibitor (inhibitos of vascular endothelial cell growth factor or vascular endothelial cell growth factor receptor; inhibitors of angiogenesis); corticosteroid anti-inflammatory drugs (e.g., SB203580); TNF-convertase inhibitors; anti-IL-12 antibodies; interleukin-11 (see e.g., Arthritis & Rheumatism (1996) Vol. 39, No. 9 (supplement), S296); interleukin-13 (see e.g., Arthritis & Rheumatism (1996) vol. 39, No. 9 (supplement), S308); interleukin-17 inhibitors (see e.g., Arthritis & Rheumatism (1996) Vol. 39, No. 9 (supplement), S120); gold; penicillamine; chloroquine; hydroxychloroquine; chlorambucil; cyclophosphamide; cyclosporine; total lymphoid irradiation; anti-thymocyte globulin; anti-CD4 antibodies; CD5-toxins; orally-administered peptides and collagen; lobenzarit disodium; Cytokine Regulating Agents (CRAs) HP228 and HP466 (Houghten Pharmaceuticals, Inc.); ICAM-1 antisense phosphorothioate oligodeoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids; see e.g., DeLuca et al. (1995) Rheum. Dis. Clin. North Am. 21:759-777); auranofin; phenylbutazone; meclofenamic acid; flufenamic acid; intravenous immune globulin; zileuton; mycophenolic acid (RS-61443); tacrolimus (FK-506); sirolimus (rapamycin); amiprilose (therafectin); cladribine (2-chlorodeoxyadenosine); and azaribine.

Nonlimiting examples of therapeutic agents for inflammatory bowel disease with which a low dose of an antibody, antibody portion, other TNFα inhibitor of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; CDP-571/BAY-10-3356 (humanized anti-TNFα antibody; Celltech/Bayer); cA2 (chimeric anti-TNFα antibody; Centocor); 75 kdTNFR-IgG (75 kD TNF receptor-IgG fusion protein; Immunex; see e.g., Arthritis & Rheumatism (1994) Vol. 37, S295; J. Invest. Med. (1996) Vol. 44 235A); 55 kdTNFR-IgG (55 kD TNF receptor-IgG fusion protein; Hoffmann-LaRoche); interleukin-10 (SCH 52000; Schering Plough); IL-4; IL-10 and/or IL-4 agonists (e.g., agonist antibodies); interleukin-11; glucuronideor dextran-conjugated prodrugs of prednisolone, dexamethasone or budesonide; ICAM-1 antisense phosphorothioate oligodeoxynucleotides (ISIS 2302; Isis Pharmaceuticals, Inc.); soluble complement receptor 1 (TP10; T Cell Sciences, Inc.); slow-release mesalazine; methotrexate; antagonists of Platelet Activating Factor (PAF); ciprofloxacin; and lignocaine.

Nonlimiting examples of therapeutic agents for multiple sclerosis with which a low dose of an antibody, antibody portion, or other TNFα inhibitors of the invention can be combined include the following: corticosteroids; prednisolone; methylprednisolone; azathioprine; cyclophosphamide; cyclosporine; methotrexate; 4-aminopyridine; tizanidine; interferon-β1a (Avonex™; Biogen); interferon-β1b (Betaseron™; Chiron/Berlex); Copolymer 1 (Cop-1; Copaxone™; Teva Pharmaceutical Industries, Inc.); hyperbaric oxygen; intravenous immunoglobulin; clabribine; CDP-571/BAY-10-3356 (humanized anti-TNFα antibody; Celltech/Bayer); cA2 (chimeric anti-TNFα antibody; Centocor); 75 kdTNFR-IgG (75 kD TNF receptor-IgG fusion protein; Immunex; see e.g., *Arthritis & Rheumatism* (1994) Vol. E, S295; *J. Invest. Med.* (1996) Vol. 44 235A); 55 kdTNFR-IgG (55 kD TNF receptor-IgG fusion protein; Hoffmann-LaRoche); IL-10; IL-4; and IL-10 and/or IL-4 agonists (e.g., agonist antibodies).

Nonlimiting examples of therapeutic agents for sepsis with which a low dose of an antibody, antibody portion, or other TNFα inhibitor, of the invention can be combined include the following: hypertonic saline solutions; antibiotics; intravenous gamma globulin; continuous hemofiltration; carbapenems (e.g., meropenem); antagonists of cytokines such as TNFα, IL-1β, IL-6 and/or IL-8; CDP-571/BAY-10-3356 (humanized anti-TNFα antibody; Celltech/Bayer); cA2 (chimeric anti-TNFα antibody; Centocor); 75 kdTNFR-IgG (75 kD TNF receptor-IgG fusion protein; Immunex; see e.g., *Arthritis & Rheumatism* (1994) Vol. 37 S295; J. Invest. Med. (1996) Vol. 44, 235A); 55 kdTNFR-IgG (55 kD TNF receptor-IgG fusion protein; Hoffmann-LaRoche); Cytokine Regulating Agents (CRAs) HP228 and HP466 (Houghten Pharmaceuticals, Inc.); SK&F 107647 (low molecular peptide; SmithKline Beecham); tetravalent guanylhydrazone CNI-1493 (Picower Institute); Tissue Factor Pathway Inhibitor (TFPI; Chiron); PHP (chemically modified hemoglobin; APEX Bioscience); iron chelators and chelates, including diethylenetriamine pentaacetic acid—iron (III) complex (DTPA iron (III); Molichem Medicines); lisofylline (synthetic small molecule methylxanthine; Cell Therapeutics, Inc.); PGG-Glucan (aqeuous soluble β1,3glucan; Alpha-Beta Technology); apolipoprotein A-1 reconstituted with lipids; chiral hydroxamic acids (synthetic antibacterials that inhibit lipid A biosynthesis); anti-endotoxin antibodies; E5531 (synthetic lipid A antagonist; Eisai America, Inc.); rBPI$_{21}$ (recombinant N-terminal fragment of human Bactericidal/Permeability-Increasing Protein); and Synthetic Anti-Endotoxin Peptides (SAEP; BiosYnth Research Laboratories);

Nonlimiting examples of therapeutic agents for adult respiratory distress syndrome (ARDS) with which a low dose of an antibody, antibody portion, or other TNFα inhibitor of the invention can be combined include the following: anti-IL-8 antibodies; surfactant replacement therapy; CDP-571/BAY-10-3356 (humanized anti-TNFα antibody; Celltech/Bayer); cA2 (chimeric anti-TNFα antibody; Centocor); 75 kdTNFR-IgG (75 kD TNF receptor-IgG fusion protein; Immunex; see e.g., *Arthritis & Rheumatism* (1994) Vol. E, S295; *J. Invest. Med.* (1996) Vol. 44, 235A); and 55 kdTNFR-IgG (55 kD TNF receptor-IgG fusion protein; Hoffmann-LaRoche).

Other therapeutic agents include chemotherapeutic agents, radiation therapy, neuroprotective agents and antiinfective agents which may be useful for treatment of a particular disorder for which TNFα activity is detrimental.

The language "chemotherapeutic agent" is intended to include chemical reagents which inhibit the growth of proliferating cells or tissues wherein the growth of such cells or tissues is undesirable or otherwise treat at least one resulting symptom of such a growth. Chemotherapeutic agents are well known in the art (see e.g., Gilman A. G., et al., *The Pharmacological Basis of Therapeutics,* 8th Ed., Sec 12:1202-1263 (1990)), and are typically used to treat neoplastic diseases. Examples of chemotherapeutic agents include: bleomycin, docetaxel (Taxotere®), doxorubicin, edatrexate, etoposide, finasteride (Proscar®), flutamide (Eulexin®), gemcitabine (Gemzar®), goserelin acetate (Zoladex®), granisetron (Kytril®), irinotecan (Campto/Camptosar®), ondansetron (Zofran®), paclitaxel (Taxol®), pegaspargase (Oncaspar®), pilocarpine hydrochloride (Salagen®), porfimer sodium (Photofrin®), interleukin-2 (Proleukin®), rituximab (Rituxan®), topotecan (Hycamtin®), trastuzumab (Herceptin®), tretinoin (Retin-A®), Triapine, vincristine, and vinorelbine tartrate (Navelbine®).

Other examples of chemotherapeutic agents include alkylating drugs such as Nitrogen Mustards (e.g., Mechlorethamine (HN$_2$), cyclophosphamide, ifosfamide, melphalan (L-sarcolysin), chlorambucil, etc.); ethylenimines, methylmelamines (e.g., Hexamethylmelamine® (altretamine), thiotepa, etc.); Alkyl Sulfonates (e.g., busulfan, etc.), nitrosoureas (e.g., carmustine (BCNU), lomustine (CCNU), semustine (methyl-CCNU), streptozocin (streptozotocin), etc.), triazenes (e.g., decarbazine (DTIC; dimethyltriazenoimi-dazolecarboxamide)), alkylators (e.g., cis-diamminedichloroplatinum II (CDDP)), etc.

Other examples of chemotherapeutic agents include antimetabolites such as folic acid analogs (e.g., methotrexate (amethopterin)); pyrimidine analogs (e.g., fluorouracil ('5-fluorouracil; 5-FU); floxuridine (fluorode-oxyuridine); FUdr; cytarabine (cyosine arabinoside), etc.); purine analogs (e.g., mercaptopurine (6-mercaptopurine; 6-MP); thioguanine (6-thioguanine; TG); and pentostatin (2'-deoxycoformycin)), etc.

Other examples of chemotherapeutic agents also include vinca alkaloids (e.g., vinblastine (VLB) and vincristine); topoisomerase inhibitors (e.g., etoposide, teniposide, Camptothecin™, topotecan, 9-amino-campotothecin CPT-11, etc.); antibiotics (e.g., Dactinomycin (actinomycin D), Adriamycin® (doxorubicin), daunorubicin, doxorubicin, bleomycin, plicamycin (mithramycin), mitomycin (mitomycin C), Taxol® (paclitaxel), Taxotere® (docetaxel), etc.); enzymes (e.g., L-asparaginase); and biological response modifiers (e.g., interferon-; interleukin 2, etc.). Other chemotherapeutic agents include cis-diaminedichloroplatinum 11 (CDDP); carboplatin; anthracendione (e.g., mitoxantrone); hydroxyurea; procarbazine (N-methylhydrazine); and adrenocortical suppressants (e.g., mitotane, aminoglutethimide, etc.).

Other chemotherapeutic agents include adrenocorticosteroids (e.g., prednisone); progestins (e.g., hydroxyprogesterone caproate,; medroxyprogesterone acetate, megestrol acetate, etc.); estrogens (e.g., diethylstilbestrol; ethenyl estradiol, etc.); antiestrogens (e.g. tamoxifen, etc.); androgens (e.g., testosterone propionate, fluoxymesterone, etc.); antiandrogens (e.g., flutamide); and gonadotropin-releasing hormone analogs (e.g., leuprolide).

The language "radiation therapy" includes the application of a genetically and somatically safe level of x-rays, both localized and non-localized, to a subject to inhibit, reduce, or prevent symptoms or conditions associated with cancer or other undesirable cell growth. The term "x-rays" includes clinically acceptable radioactive elements and isotopes thereof, as well as the radioactive emissions therefrom. Examples of the types of emissions include alpha rays, beta rays including hard betas, high energy electrons, and gamma rays. Radiation therapy is well known in the art (see e.g., Fishbach, F., *Laboratory Diagnostic Tests,* 3rd Ed., Ch. 10: 581-644 (1988)), and is typically used to treat neoplastic diseases.

Examples of neuroprotective agents include, but are not limited to, compounds that remove protein build up (e.g., geldanamycin), anti-inflammatory agents (e.g., glucocorticoids, non-steroidal anti-inflammatory drugs (e.g., ibuprofen, aspirin, etc.), omega-3 fatty acids (e.g., EPA, DHA, etc.), minocycline, dexanabionol, etc.), compounds that increase energy available to cells (e.g., creatine, creatine phosphate, dichloroacetate, nicotinamide, riboflavin, carnitine, etc.), anti-oxidants (e.g., plant extracts (e.g., gingko biloba), co-enzyme Q-10, vitamin E (alpha-tocopherol), vitamin C (ascorbic acid), vitamin A (beta-carotene), selenium, lipoic acid, selegine, etc.), anti-glutamate therapies (e.g., remacemide, riluzole, lamotrigine, gabapentin, etc.), GABA-ergic therapies (e.g., baclofen, muscimol, etc.), gene transcription regulators (e.g., glucocorticoids, retinoic acid, etc.), erythropoietin, TNF-α antagonists, cholinesterase inhibitors, N-methyl-D-aspartate (NMDA) antagonists, opiod antagonists, neuronal membrane stabilizers (e.g., CDP-choline, etc.), calcium and sodium channel blockers, prednisone, etc.

Antiinfective agents include those agents known in the art to treat viral, fungal, parasitic or bacterial infections.

This invention is further illustrated by the following examples which should not be construed as limiting. The contents of all references, patents and published patent applications cited throughout this application are hereby incorporated by reference.

Example 1

Study of Efficacy of D2E7 Administered in Low Doses

Studies were performed to determine the efficacy of D2E7, infliximab, and etanercept at low doses in preventing polyarthritis using the transgenic (Tg197) murine model of rheumatoid arthritis (RA). Infliximab is a human-mouse chimeric antibody, and etanercept is a p75 TNF receptor construct. D2E7 is a fully human antibody derived from a human immunoglobulin gene library. Transgenic mice, Tg197 carry the human TNFα gene and spontaneously develop a disease similar to human rheumatoid arthritis (Keffer, J. et al, 1991, *EMBO J.* 10:4025). Signs of arthritic disease, including rheumatoid arthritis, include slower weight gain, joint distortion and swelling, joint deformation and ankylosis and impaired movement. Histopathological findings include hyperplasia of the synovial membrane, leukocyte infiltration, pannus formation, articular cartilage and bone destruction. Administration of anti-TNF agents prevents the development of polyarthritis in a dose dependent manner.

A. Comparison of Binding Characteristics of D2E7, Remicade® (infliximab), and Enbrel® (Etanercept)

Infliximab (Remicade®) and Etanercept (Enbrel®) are two anti-TNF drugs approved for rheumatoid arthritis. Remicade® is a human-mouse chimeric $IgG_1$ antibody and Enbrel® is a fusion protein made up of extra-cellular domain of the p75 TNF receptor and the constant region of $IgG_1$ molecule. D2E7 is a fully human antibody of the $IgG_1$, kappa class selected from human immunoglobulin gene libraries. All three anti-TNF agents bind to human TNF with relatively similar potency. The intrinsic affinities of D2E7, Remicade® and Enbrel® for TNF are $8.6 \times 10^{-11}$, $9.5 \times 10^{-11}$ and $15.7 \times 10^{-11}$ M (Kd values), respectively. The kinetics of binding to TNF are similar for the antibodies D2E7 and Remicade®. Enbrel®, on the other hand, binds to and dissociates from TNF fast. Thus, the 16 minute half-life of Enbrel®:TNF complex is considerably shorter than the 184 and 255 minute half-lives for Remicade® and D2E7:TNF complexes, respectively.

A BIAcore 3000 instrument was used to derive kinetic parameters of binding between human TNF and anti-TNF agents. Biosensor chips were covalently coupled with a goat anti-human Fc antibody. Anti-TNF agents (D2E7, Remicade® and Enbrel®) were then captured on the chips and varying concentrations of huTNF were added. Binding data were analyzed to derive the kinetic parameters, which are described in Table 1.

TABLE 1

| Binding of D2E7, Remicade ®, or Enbrel ® to human TNF | | | |
|---|---|---|---|
| Agent | On-rate ($M^{-1}s^{-1}$) | Off-rate ($s^{-1}$) | Kd (M) |
| D2E7 | $5.37 \times 10^5$ | $4.53 \times 10^{-5}$ | $8.56 \times 10^{-11}$ |
| Remicade ® | $6.71 \times 10^5$ | $6.29 \times 10^{-5}$ | $9.45 \times 10^{-11}$ |
| Enbrel ® | $4.47 \times 10^6$ | $7.02 \times 10^{-4}$ | $1.57 \times 10^{-10}$ |

B. Prevention of Arthritic Symptoms

Tg197 Mice were used as a model for studying the effects of a low dose regimen of D2E7, Remicade®, and Enbrel® on relieving symptoms commonly associated with rheumatoid arthritis. Human TNF transgenic mice were identified and verified by PCR. From the first week of age, separate litters of Tg197 mice were assigned to different study groups. Tg197 mice heterozygous for the human TNF gene received weekly intraperitoneal doses of D2E7, Remicade® or Enbrel®. Each drug treatment dose group consisted of mice from a single litter. The control group received the phosphate buffered saline diluent and consisted of mice from 4 litters. Weights of animals in each group were recorded weekly prior to dosing. Each group received one i.p. injection per week as follows:

| Vehicle control | | |
|---|---|---|
| D2E7, 10 mg/kg | Remicade ®, 10 mg/kg | Enbrel ®, 10 mg/kg |
| D2E7, 5 mg/kg | Remicade ®, 5 mg/kg | Enbrel ®, 5 mg/kg |
| D2E7, 1 mg/kg | Remicade ®, 1 mg/kg | Enbrel ®, 1 mg/kg |
| D2E7, 0.5 mg/kg | Remicade ®, 0.5 mg/kg | Enbrel ®, 0.5 mg/kg |
| D2E7, 0.1 mg/kg | Remicade ®, 0.1 mg/kg | Enbrel ®, 0.1 mg/kg |
| D2E7, 0.01 mg/kg | Remicade ®, 0.01 mg/kg | Enbrel ®, 0.01 mg/kg |

Arthritic scores in each group were recorded each week using the following scoring system:
 0 no arthritis
 1 mild arthritis (joint distortion)
 2 moderate arthritis (swelling, joint deformation)
 3 severe arthritis (ankylosis on flexion and severely impairment movement)

Figure 2:
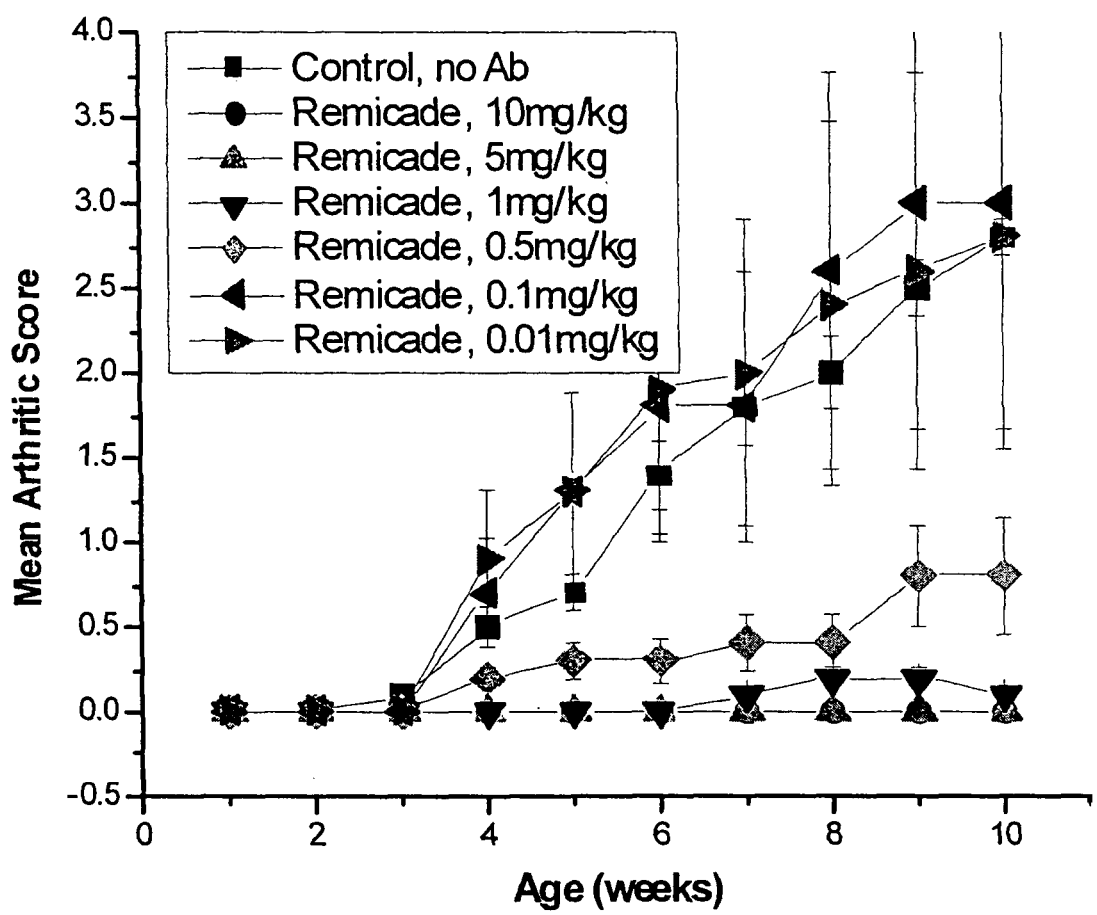
FIG. 2 shows arthritic scores of each mouse in the treatment groups receiving different doses of Remicade® (infliximab). Arthritic scores were recorded weekly starting at 1 week of age. For each treatment group, mean±standard error of arthritis scores are indicated in the graph. The treatment groups were as follows: Control group: 11 female, 9 male mice (n=20); 10 mg/kg dose group: 4 female, 1 male mice (n=5); 5 mg/kg dose group: 3 female, 4 male mice (n=7); 1 mg/kg dose group: 6 female, 2 male mice (n=8); 0.5 mg/kg dose group: 4 female, 2 male mice (n=6); 0.1 mg/kg dose group: 1 female, 4 male mice (n=5); 0.01 mg/kg dose group: 2 female, 3 male mice (n=5).
Figure 3:
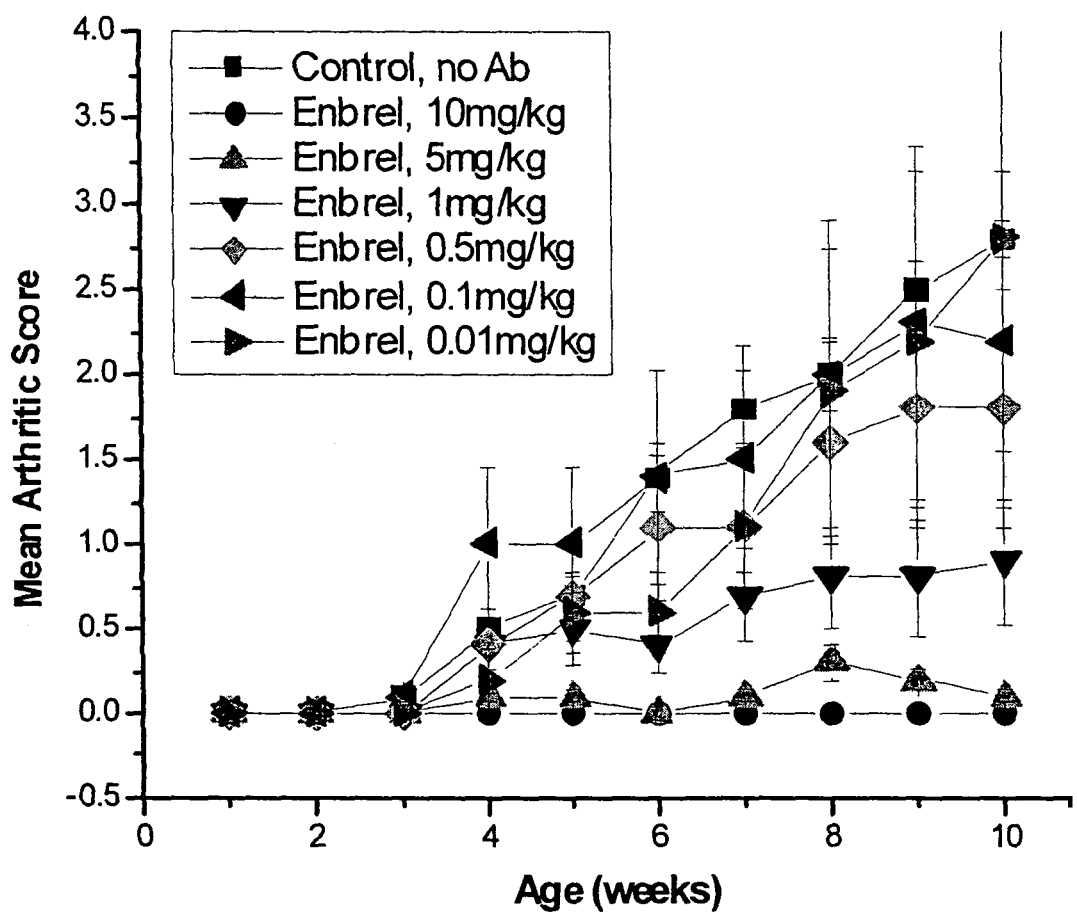
FIG. 3 shows arthritic scores of each mouse in the treatment groups receiving different doses of Enbrel® (etanercept). Arthritic scores were recorded weekly starting at 1 week of age. For each treatment group, mean±standard error of arthritis scores are indicated in the graph. The treatment groups were as follows: Control group: 11 female, 9 male mice (n=20); 10 mg/kg dose group: 3 female, 2 male mice (n=5); 5 mg/kg dose group: 3 female, 3 male mice (n=6); 1 mg/kg dose group: 5 female, 1 male mice (n=6); 0.5 mg/kg dose group: 4 female, 3 male mice (n=7); 0.1 mg/kg dose group: 2 female, 3 male mice (n=5); 0.01 mg/kg dose group: 2 female, 4 male mice (n=6).
Figure 4:
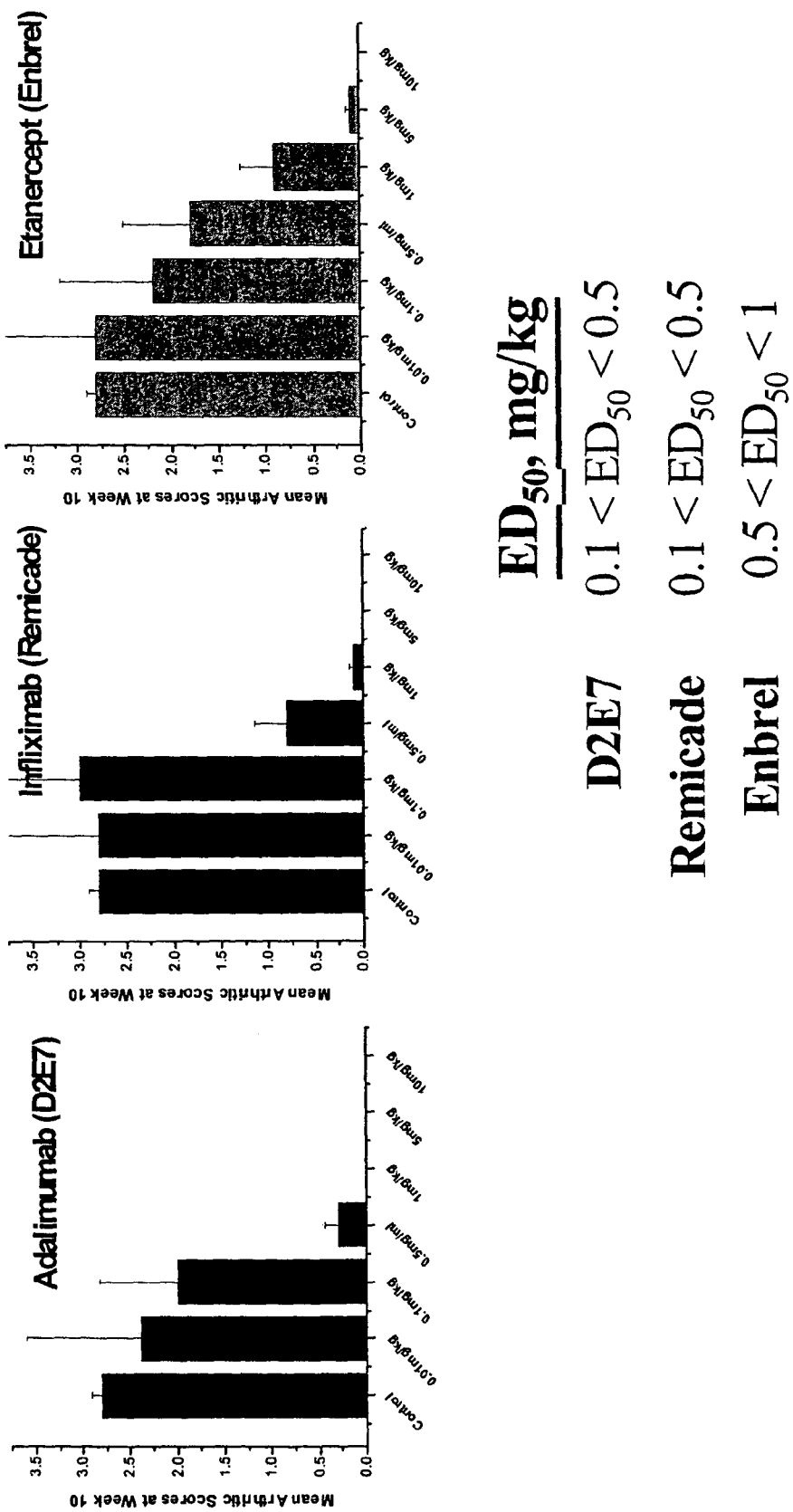
FIG. 4 shows final arthritic scores in D2E7, Remicade® (infliximab), and Enbrel® (etanercept) treated huTNF-Tg197 mice at 10 weeks of age.

Treatment continued for 10 weeks. Results from the scoring assay are shown in FIGS. 1, 2, and 3. FIG. 4 shows the final arthritic score for the three antibodies in treated Tg197 mice at week 10. The results show that higher doses of Enbrel® were needed to prevent the development of arthritic scores. The $ED_{50}$ value for Enbrel® was close to 1 mg/kg; whereas the $ED_{50}$ value for D2E7 and Remicade® was below 0.5 mg/kg. Between the two antibodies, D2E7 offered more protection than Remicade® at the same doses. Furthermore, the onset of disease was delayed in mice treated with 0.5 mg/kg of D2E7 up to 5 weeks, and with mice treated with 0.1 mg/kg doses of D2E7 up to 4 weeks (FIG. 1). In contrast, the onset of disease was delayed in mice treated with either 0.1 mg/kg or 0.5 mg/kg of Remicade® for only 3 weeks (FIG. 2).

In sum, all three agents, D2E7, Remicade®, and Enbrel® prevented the development of arthritis in Tg197 mice in a dose dependent fashion. Treated mice had lower arthritic scores and less inflammation and joint damage and gained more weight than the untreated mice. The pattern of response was similar for all three TNF antagonists, but the degree of protection varied among the three agents. Although the highest, saturating doses did not allow distinction between the agents, the potency of protection at intermediate doses was greatest for D2E7 treated mice, than for infliximab (Remicade®), and the least for etanercept (Enbrel®) treated mice.

C. Analysis of Circulating huTNF levels in Treated Mice

Figure 6:
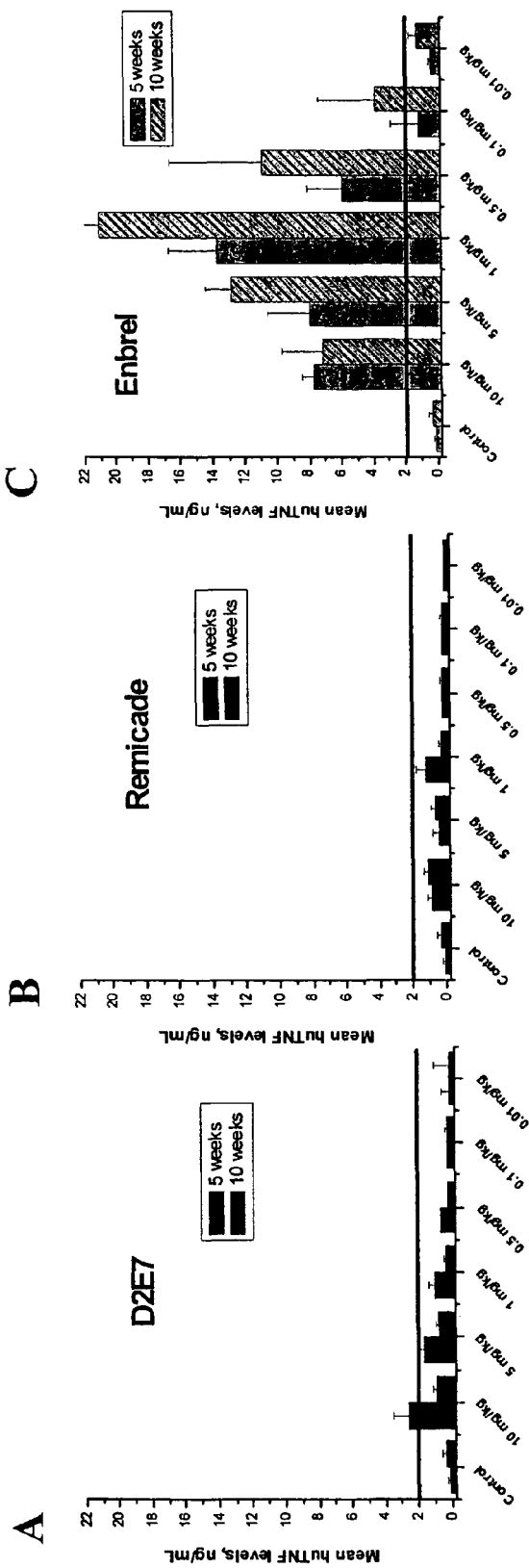
FIGS. 6A, 6B, and 6C show circulating huTNF levels in D2E7, Remicade® (infliximab), and Enbrel® (etanercept) treated huTNF-Tg197 mice.

Blood was collected at 5 and 10 weeks during the study. Serum was prepared and the levels of human TNF were determined by the Medgenix human TNF ELISA kit. TNF levels were measured for each mouse in treatment groups. Results from the study are shown in FIG. 6. For each treatment group, mean±standard error of TNF levels are indicated in the graph. A solid line at each graph is drawn at 2 ng/mL TNF level for orientation purpose. In the untreated group, serum huTNF levels were low, 0.1 and 0.2 ng/mL at 5 and 10 weeks, respectively. Weekly administration of anti-TNF agents resulted in sequestration of TNF in the serum. The levels of serum huTNF were similar for D2E7 or Remicade® treated mice. The average huTNF levels decreased from 2 to 0.1 ng/mL as a function of administered dose. Enbrel® treated mice, on the other hand, had much higher serum huTNF, reaching levels of 20 ng/mL.

In sum, measurement of human TNF by Medgenix ELISA, which detects both free and bound TNF, indicated that the anti-TNF agents were sequestering TNF into complexes. There were detectable levels of TNF in the serum of treated mice in contrast to very low levels in untreated mice. Interestingly, the level of noncleared TNF complexes for etanercept was 10-fold higher than in mice treated with infliximab or D2E7. Delayed TNF clearance with etanercept has been noted in published animal models and clinical studies.

D. Microscopic Analysis of Treated Mice

Following the 10 week treatment, all mice were sacrificed. Right and left hind limbs were harvested from two mice in each treatment group. Limbs were fixed in 10% neutral buffered formalin and then decalcified. Three consecutive sections from each limb sample were mounted on slides and the coded slides were sent for an independent evaluation by a pathologist.

Slides were stained with hematoxylin/eosin. The pathologist scored each slide with respect to severity of vascularity, inflammation, cartilage and bone erosion on a scale of 1-4. Results are shown in Table 2 below:

TABLE 2

Approximate $ED_{50}$ (mg/kg) values of D2E7, Remicade ® or Enbrel ® for prevention of microscopic signs of arthritis in Tg197 mice

|  | D2E7 $ED_{50}$, mg/kg | Remicade ® $ED_{50}$, mg/kg | Enbrel ® $ED_{50}$, mg/kg |
| --- | --- | --- | --- |
| Inflammation | 0.1 | 0.5 | 0.5 |
| Vascularity | 0.1 | 0.1 | $1 < ED_{50} < 5$ |
| Cartilage Erosion | $0.01 < ED_{50} < 0.1$ | $0.1 < ED_{50} < 0.5$ | 0.5 |
| Bone Erosion | $0.01 < ED_{50} < 0.1$ | $0.1 < ED_{50} < 0.5$ | $0.5 < ED_{50} < 1$ |

Figure 5:
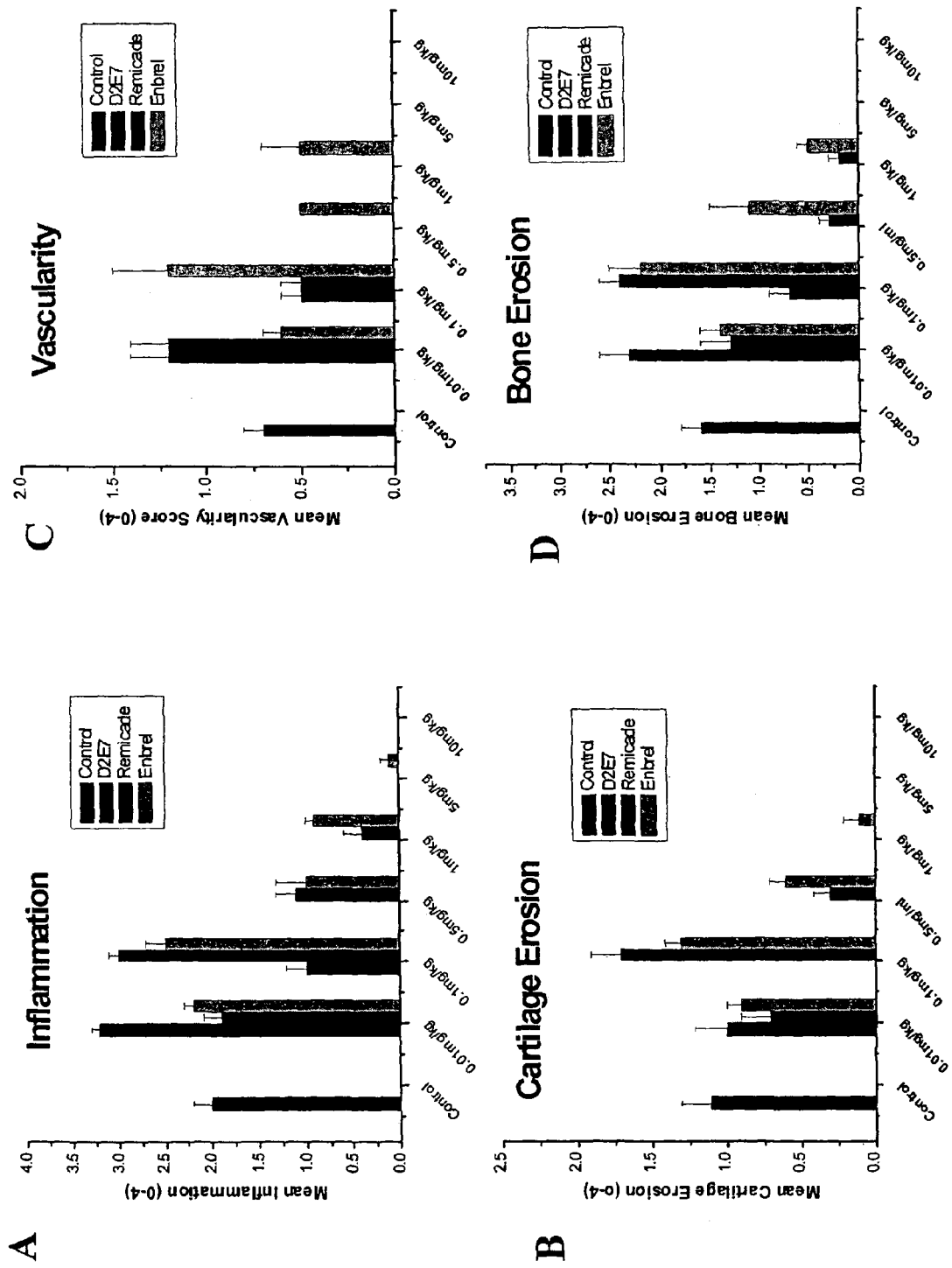
FIGS. 5A-D show a histopathological evaluation of various tissues taken from arthritic joints.

Results from this experiment are also shown in FIG. 5. In FIG. 5, three slides from each limb were examined; thus, 6 slides per mouse and 12 slides per treatment group were scored for histopathology. For each treatment group, mean±standard deviation of histopathology scores are indicated in the graph. Most of the lesions were associated with ankle joints and all appeared symmetrical (i.e. similar scores for the left and right limbs for a given mouse). Cartilage degradation resulted mostly from endosteal erosive lesions and was generally less extensive than bone erosion. Inflammation was predominantly mononuclear cells with few PMNs, but no dense PMN loci.

The difference among the three anti-TNF agents was most pronounced in microscopic signs of disease activity in the arthritic joints than the external manifestations measured as arthritic scores. Bone erosion in the joints was completely abolished by 0.5 mg/kg dose of D2E7. In order to achieve the same effect a much higher dose of Remicade® or Enbrel®, 5 mg/kg, was needed. Cartilage erosion in the joints was completely abolished by 0.1 mg/kg dose of D2E7. In order to achieve the same effect a much higher dose of Remicade®, 1 mg/kg, or Enbrel®, 5 mg/kg, was needed. Inflammation in the joints was completely abolished by 0.5 mg/kg dose of D2E7. In order to achieve the same effect higher doses of other drugs were needed: 5 mg/kg for Remicade® and 10 mg/kg for Enbrel®. Vascularity in the joints was completely abolished by 0.5 mg/kg dose of D2E7 or Remicade®. In order to achieve the same effect a much higher dose of Enbrel®, 5 mg/kg, was needed.

There was a clear dose-response distinction between D2E7, infliximab and etanercept in prevention of microscopic joint damage. Whereas D2E7 completely prevented bone erosion, cartilage degradation, inflammation, and vascularity at the 0.5-mg/kg dose, both infliximab and etanercept required a dose of 1 or 5 mg/kg to reach similar levels of efficacy. In sum, in the human TNF transgenic mice, Tg197, D2E7 prevented polyarthritis more potently than did etanercept or infliximab, especially at low doses.

EQUIVALENTS

Those skilled in the art will recognize, or be able to ascertain using no more than routine experimentation, many equivalents to the specific embodiments of the invention described herein. Such equivalents are intended to be encompassed by the following claims. The contents of all references, patents and patent applications cited throughout this application are hereby incorporated by reference. The entire contents of U.S. Pat. Nos. 6,090,382 and 6,258,562 B1, and in U.S. patent application Ser. Nos. 09/540,018, and 09/801,185, are hereby incorporated herein by reference in their entirety.

The invention claimed is:

1. A method for treating arthritis comprising administering by injection to a subject an isolated fully human anti-TNFα antibody at a weekly dose of 0.1 mg/kg such that the arthritis is treated as demonstrable by mean arthritic score, wherein the anti-TNFα antibody is D2E7.

2. The method of claim 1, wherein the arthritis is rheumatoid arthritis.

3. The method of claim 1 or 2, wherein arthritis is further treated by alleviating at least one symptom selected from the group consisting of bone erosion, cartilage erosion, inflammation, and vascularity.

4. A method for alleviating at least one symptom associated with arthritis comprising administering by injection to a subject an isolated fully human anti-TNFα antibody at a weekly dose of 0.06-0.1 mg/kg, such that at least one symptom selected from the group consisting of bone erosion, cartilage erosion, inflammation, and vascularity is alleviated, as demonstrable after 10 treatments, wherein the anti-TNFα antibody is D2E7.

5. The method of claim 4, wherein the arthritis is rheumatoid arthritis.

6. The method of claim 4, wherein the symptom is further selected from the group consisting of joint distortion, swelling, joint deformation, ankylosis on flexion, and severely impaired movement.

7. The method of claim 1 or 4, wherein the anti-TNFα antibody, or an antigen-binding portion thereof, is administered with an additional therapeutic agent.

8. A method for treating rheumatoid arthritis comprising administering by injection to a subject at a weekly dose of 0.06-0.1 mg/kg of a fully human TNFα antibody such that the rheumatoid arthritis is treated, as demonstrable by mean arthritic score after 10 treatments, wherein the anti-TNFα antibody is D2E7 and wherein arthritis is treated by alleviating at least one symptom selected from the group consisting of joint distortion, swelling of the joints, joint deformation, and ankylosis on flexion.

9. The method of claim 8, wherein rheumatoid arthritis is further treated by alleviating at least one symptom selected from the group consisting of bone erosion, cartilage erosion, inflammation, and vascularity.

10. A method of improving symptoms in the joints of a subject having arthritis comprising administering by injection to the subject a weekly dose of 0.06-0.1 mg/kg of a fully human anti-TNFα antibody such that at least one symptom selected from the group consisting of inflammation, cartilage erosion, bone erosion, and vascularity is improved, wherein the anti-TNFα antibody is D2E7.

11. The method of claim 4, 8, or 10, wherein the low dose is 0.1 mg/kg.

12. The method of claim 4, 8, or 10, wherein the low dose is 0.09-0.1 mg/kg.

* * * * *